US011180578B2

(12) United States Patent
Masere et al.

(10) Patent No.: US 11,180,578 B2
(45) Date of Patent: Nov. 23, 2021

(54) POLYMERIZATION INHIBITOR AND RETARDER COMPOSITIONS WITH AMINE STABILIZER

(71) Applicant: Ecolab USA Inc., St. Paul, MN (US)

(72) Inventors: Jonathan Masere, Richmond, TX (US); Andrew R. Neilson, Richmond, TX (US); Bassam Alnasleh, Sugar Land, TX (US); Ramon Colorado, Jr., Stafford, TX (US)

(73) Assignee: Ecolab USA Inc., St. Paul, MN (US)

( * ) Notice: Subject to any disclaimer, the term of this patent is extended or adjusted under 35 U.S.C. 154(b) by 70 days.

(21) Appl. No.: 16/510,053

(22) Filed: Jul. 12, 2019

(65) Prior Publication Data
US 2020/0017610 A1 Jan. 16, 2020

Related U.S. Application Data

(60) Provisional application No. 62/697,715, filed on Jul. 13, 2018.

(51) Int. Cl.
C08F 2/40 (2006.01)
C08F 12/30 (2006.01)
C08F 12/36 (2006.01)
C08F 20/06 (2006.01)
C08F 20/18 (2006.01)
C08F 20/44 (2006.01)
C08F 26/06 (2006.01)
C08K 5/00 (2006.01)
C08K 5/08 (2006.01)
C08K 5/17 (2006.01)
C08K 5/3435 (2006.01)

(52) U.S. Cl.
CPC ............... C08F 2/40 (2013.01); C08F 12/30 (2013.01); C08F 12/36 (2013.01); C08F 20/06 (2013.01); C08F 20/18 (2013.01); C08F 20/44 (2013.01); C08F 26/06 (2013.01); C08K 5/005 (2013.01); C08K 5/08 (2013.01); C08K 5/17 (2013.01); C08K 5/3435 (2013.01)

(58) Field of Classification Search
CPC .. C08F 2/40; C08F 12/30; C08F 12/36; C08F 20/06; C08F 20/18; C08F 20/44; C08F 26/06; C08K 5/005; C08K 5/08; C08K 5/17; C08K 5/3435; C08K 5/32; C07C 51/50; C07C 7/20; C07B 63/04; C07D 211/94
See application file for complete search history.

(56) References Cited

U.S. PATENT DOCUMENTS

| | | | |
|---|---|---|---|
| 4,670,131 | A | 6/1987 | Ferrell |
| 5,196,589 | A | 3/1993 | O'Lenick, Jr. et al. |
| 5,583,247 | A | 12/1996 | Nesvadba et al. |
| 5,616,774 | A | 4/1997 | Evans et al. |
| 6,024,894 | A | 2/2000 | Arhancet |
| 6,403,850 | B1 | 6/2002 | Benage et al. |
| 6,579,442 | B2 | 6/2003 | Eldin |
| 6,653,414 | B2 | 11/2003 | Benage et al. |
| 6,926,820 | B2 | 8/2005 | Eldin et al. |
| 7,022,220 | B2 | 4/2006 | Benage et al. |
| 7,045,647 | B2 | 5/2006 | Benage |
| 7,128,826 | B2 | 10/2006 | Eldin et al. |
| 7,473,795 | B2 | 1/2009 | Benage |
| 7,553,896 | B2 | 6/2009 | Ma et al. |
| 7,651,635 | B1 | 1/2010 | Lewis |
| 7,696,290 | B2 | 4/2010 | Kosover et al. |
| 7,723,398 | B2 | 5/2010 | Ilg et al. |
| 7,728,083 | B1 | 6/2010 | Kosover et al. |
| 7,943,809 | B2 | 5/2011 | Benage et al. |
| 8,766,027 | B1 | 7/2014 | Subramaniyam |
| 8,884,038 | B2 | 11/2014 | Masere |
| 8,901,362 | B2 | 12/2014 | Link |
| 9,090,526 | B2 | 7/2015 | Masere |
| 9,133,288 | B2 | 9/2015 | Loyns et al. |
| 9,206,268 | B2 | 12/2015 | Link et al. |
| 9,217,107 | B2 | 12/2015 | Subramaniyam |
| 9,228,126 | B2 | 1/2016 | Subramaniyam |
| 9,234,057 | B2 | 1/2016 | Subramaniyam |
| 9,266,797 | B2 | 2/2016 | Colorado, Jr. et al. |
| 9,334,445 | B2 | 5/2016 | Subramaniyam |
| 9,493,382 | B2 | 11/2016 | Rinker et al. |
| 9,598,333 | B2 | 3/2017 | Subramaniyam |

(Continued)

FOREIGN PATENT DOCUMENTS

EP 2993164 A1 3/2016
WO 9948996 A1 9/1999
(Continued)

OTHER PUBLICATIONS

WHO; N-nitrosodiphenylamine Data Sheet, 2003, p. 1-2.*
(Continued)

Primary Examiner — Robert S Jones, Jr.
(74) Attorney, Agent, or Firm — Kagan Binder, PLLC

(57) ABSTRACT

Described are compositions and methods for inhibiting polymerization of a monomer (e.g., styrene) composition, which use an N—O polymerization inhibitor, a quinone methide polymerization retarder, and an amine stabilizer having a primary and/or secondary amine group. In a mixture, the amine-based stabilizer can prevent antagonistic effects and can provide greater antipolymerant activity. In turn, the mixture inhibits apparatus fouling and improves the purity of monomer streams.

22 Claims, 2 Drawing Sheets

(56) References Cited

U.S. PATENT DOCUMENTS

| | | |
|---|---|---|
| 9,957,209 B2 | 5/2018 | Masere et al. |
| 10,138,183 B2 | 11/2018 | Rinker et al. |
| 2003/0047439 A1* | 3/2003 | Benage ............... C07C 253/32 203/7 |
| 2004/0010159 A1* | 1/2004 | Benage ............... C09K 15/08 558/306 |
| 2004/0034247 A1 | 2/2004 | Eldin |
| 2005/0113625 A1 | 5/2005 | Benage et al. |
| 2006/0020089 A1 | 1/2006 | Merrill |
| 2006/0163539 A1 | 7/2006 | Nakajima et al. |
| 2006/0178489 A1* | 8/2006 | Kosover ............... C07C 7/20 526/82 |
| 2010/0168434 A1 | 7/2010 | Loyns et al. |
| 2011/0230588 A1 | 9/2011 | Devlin et al. |
| 2015/0080501 A1 | 3/2015 | Khalyavina et al. |
| 2015/0361013 A1 | 12/2015 | Guliashvili et al. |
| 2016/0083315 A1 | 3/2016 | Subramaniyam |
| 2016/0304417 A1 | 10/2016 | Masere et al. |
| 2018/0361319 A1 | 12/2018 | Boam et al. |

FOREIGN PATENT DOCUMENTS

| | | |
|---|---|---|
| WO | 0036052 | 6/2000 |
| WO | 0233025 A2 | 4/2002 |
| WO | 2006111494 A1 | 10/2006 |
| WO | 2012173909 A2 | 12/2012 |
| WO | 2012173925 A2 | 12/2012 |
| WO | 2013054353 A1 | 4/2013 |
| WO | 2013102930 A1 | 7/2013 |
| WO | 2013116611 A1 | 8/2013 |
| WO | 2014030131 A1 | 2/2014 |
| WO | 2014155248 A1 | 10/2014 |
| WO | 2016172076 A1 | 10/2016 |
| WO | 2017137924 A1 | 8/2017 |

OTHER PUBLICATIONS

SIRC; Styrene: Chemical Identity & Physical Properties, 2014, p. 1.*

Dow; Diethylenetriamine Technical Data, p. 1-2, retrieved Dec. 11, 2020.*

ThermoFisher; Isoprene Safety Data Sheet, 2019, p. 1-8.*

Ohkatsu et al. (2007) "Interaction between Nitroxide of Hindered Amine Light Stabilizers and Phenol", Journal of the Japan Petroleum Institute, 50(2):87-93.

Motyakin, M.V., et al. (2004) "Inhibitor radicals in styrene polymerization", Journal of Applied Polymer Science, 91:1599-1603.

Yachigo, S., et al. (1992) "Studies on polymer stabilizers. Part IV. Prevention of oxidative discoloration", Polymer Degradation and Stability, 37:107-113.

* cited by examiner

POLYMERIZATION INHIBITOR AND RETARDER COMPOSITIONS WITH AMINE STABILIZER

CROSS REFERENCE TO RELATED APPLICATIONS

This application claims the benefit of U.S. Provisional Patent Application Ser. No. 62/697,715, filed Jul. 13, 2018, the disclosure of which is incorporated by reference herein in its entirety.

TECHNICAL FIELD

The invention is directed to compositions and use of an amine stabilizer compound in combination with a polymerization inhibitor and retarder for inhibiting premature polymerization of monomers.

BACKGROUND

Ethylenically unsaturated monomers, such as vinyl aromatic monomers like styrene, can be present in processing streams or in refined products made by various chemical industrial processes. However, these monomer types may undesirably polymerize through radical polymerization especially at elevated temperature. As a result, solid deposits of polymer can form on the surface of the process equipment during industrial manufacture, processing, handling, or storage. The resulting polymers can be problematic and lead to equipment "fouling" and product contamination. Accordingly, this can necessitate treating the apparatus to remove the polymer, or may necessitate processing steps to remove the polymer from compositions streams or stored compositions. These undesirable polymerization reactions result in a loss in production efficiency because they consume valuable reagents and additional steps may be required to clean equipment and/or to remove the undesired polymers. Undesired polymerization reactions are particularly problematic in compositions having vinyl aromatic monomers.

To minimize undesired polymerization reactions, compounds that act as antipolymerants are often added to process streams or stored compositions. Two categories of antipolymerants have been developed to minimize unwanted polymerization reactions: polymerization inhibitors and polymerization retarders.

Polymerization inhibitors inhibit polymerization reactions from occurring. However, these compounds are generally consumed rapidly. For example, in cases of emergency due to mechanical or processing problems, and where more inhibitor cannot be added, previously added inhibitor will be rapidly consumed. Subsequently, unwanted polymerization reactions will then rapidly recur.

Examples of polymerization inhibitors known in the art include dialkylhydroxylamines, such as hydroxypropylhydroxylamine (HPHA), and stable nitroxide free radicals. Other inhibitors include N,N'-dialkylphenylenediamines, N,N'-diarylphenylenediamines N-aryl-N'-alkylphenylenediamines. Quinone diimide compounds are also another class of inhibitors.

Polymerization retarders, while they slow down the rate of polymerization reactions, are not as effective as polymerization inhibitors. Polymerization retarders, however, are usually not consumed as quickly as polymerization inhibitors so they tend to be more useful in cases of emergency shutdown of operations.

Retarders such as sulfur and dinitrophenol (DNP) compounds such as 2,6-dinitrophenol, 2,4-dinitrocresol, and 2-sec-butyl-4,6-dinitrophenol (DNBP) were initially used. However, DNP and sulfur retarders release $NO_x$ and $SO_x$ gases, making their use problematic. Furthermore, DNP-based retarders are highly toxic, which is a concern during handling.

One class of compounds designed to function as a safer substitute for DNP retarders is based on quinone methide chemistry. Quinone methides slow the rate of polymer formation under static conditions and do not need to be frequently re-fed into the process stream. Some quinone methide compounds, however, do not exhibit good stability. Examples of quinone methide compounds are in U.S. Pat. Nos. 4,003,800, 5,583,247, and 7,045,647.

Technical challenges remain in this area of technology relating to efficacy of polymerization inhibitors and retarders, as well as stability and safety concerns. Further, the disclosure is associated with the finding that while desirable to combine polymerization inhibitors and retarders in the same composition, mixtures often suffer from compatibility issues which reduce effectiveness of both the inhibitor and the retarder activities.

SUMMARY

Disclosed herein are compositions and methods for inhibiting polymerization of monomers in a composition that includes or that can form monomers. Compositions and methods of the disclosure use a polymerization inhibitor, a polymerization retarder, and an amine compound, wherein the amine compound acts as a stabilizer which improves the functionality of the polymerization inhibitor and stabilizer when used together. Use of the amine stabilizer of the invention can not only hinder antagonistic effects observed when the polymerization inhibitor and retarder are combined, but can allow the mixture to have greater antipolymerant activity than what is observed using the inhibitor and retarder without the amine stabilizer. The mixture of inhibitor, retarder, and amine stabilizer shows remarkable activity in inhibiting unwanted polymerization of monomers such as styrene in various applications, such as in synthesis, refinement, or storage. Polymer contamination is reduced and additional processing steps can be avoided. In addition, by inhibiting polymerization, the mixture can minimize buildup of unwanted polymer on processing or storage apparatus ("fouling"), and accordingly reduce maintenance costs of such equipment.

In embodiments, the invention provides a composition for inhibiting monomer polymerization that includes a polymerization inhibitor having an N-to-O functionality, a polymerization retarder that is a quinone methide; and a stabilizer compound having a primary amine group, secondary amine group, or both. Advantageously, these components can be combined in a single package formulation, wherein the amine stabilizer reduces or eliminates any antagonistic effects the inhibitor and retarder have on each other in mixture.

Exemplary amine stabilizers include alkylated amines, particularly amines with boiling points greater than 100° C. or greater than 150° C. The amine stabilizers can stabilize nitroxide group-containing polymerization inhibitor species such as 2,2,6,6-tetramethylpiperidinyl-1-oxyl (TEMPO).

In embodiments, the invention provides use of a polymerization inhibitor having an N-to-O bond, a retarder compound that is a quinone methide; and a stabilizer compound having a primary or secondary amine group, for inhibiting monomer polymerization in a composition, for polymerizable monomer synthesis, refining, or purification, or for polymerizable monomer storage or transport.

In embodiments, the invention provides methods of preparing compositions for inhibiting monomer polymerization. One way of making the composition involves obtaining a first composition that includes (i) an inhibitor compound that has an N-to-O moiety (ii) a stabilizer compound having a primary or secondary amine group, and then adding (iii) a retarder compound that is a quinone methide to the first composition. Another way of making the composition involves obtaining a first composition that includes (i) a retarder compound that is a quinone methide (ii) a stabilizer compound having a primary or secondary amine group, and then adding (iii) an inhibitor compound having an N-to-O bond, to the first composition. Yet another way of making the composition involves combining simultaneously or sequentially (i) a retarder compound that is a quinone methide (ii) an inhibitor compound having an N-to-O bond, and (iii) a stabilizer compound having a primary or secondary amine group to form a composition for inhibiting monomer polymerization.

In embodiments, the invention also provides a method for inhibiting the polymerization of monomers in a monomer-containing composition. The method includes a step or steps of adding components that include an inhibitor compound having an N-to-O bond, a retarder compound that is a quinone methide; and a stabilizer compound having a primary or secondary amine group, to a composition that includes polymerizable monomer, or to a composition that is capable of forming a polymerizable monomer, wherein the first composition inhibits the polymerization of the polymerizable monomer.

DETAILED DESCRIPTION

Figure 1:
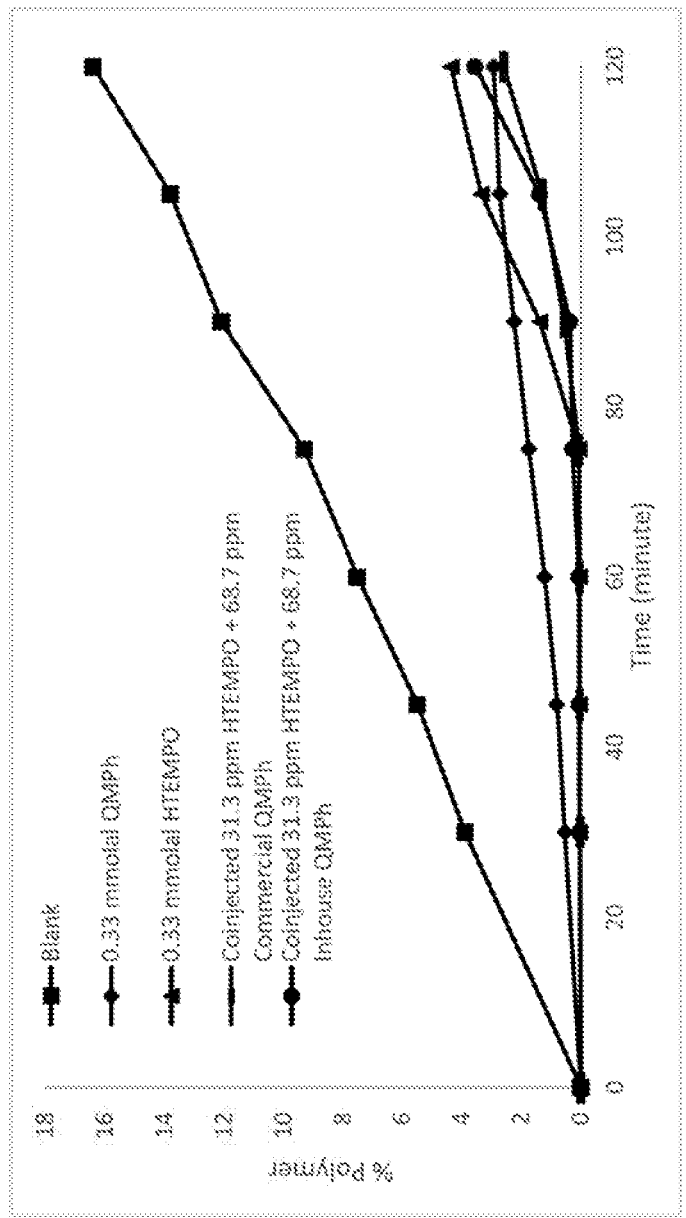
FIG. 1 is a graph of the formation of polystyrene in a styrene monomer solution over time in the presence of polymerization retarder and inhibitor co-injected or introduced separately.

Although the present disclosure provides references to preferred embodiments, persons skilled in the art will recognize that changes may be made in form and detail without departing from the spirit and scope of the invention. Reference to various embodiments does not limit the scope of the claims attached hereto. Additionally, any examples set forth in this specification are not intended to be limiting and merely set forth some of the many possible embodiments for the appended claims.

Additional advantages and novel features of the invention will be set forth in part in the description that follows, and in part will become apparent to those skilled in the art upon examination of the following, or may be learned through routine experimentation upon practice of the invention.

The disclosure provides compositions that include a polymerization inhibitor, a polymerization retarder, and an amine stabilizer for use in compositions to inhibit unwanted formation of polymer. The amine stabilizer can improve the functionality of the inhibitor and stabilizer compounds in mixture and provide better antipolymerant activity. The disclosure also provides methods which use the polymerization inhibitor, the polymerization retarder, and amine stabilizer in a method for inhibiting the polymerization of monomers in a monomer-containing composition, such as a vinyl aromatic monomer-containing composition.

A "polymerization inhibitor," in the presence of polymerizable monomers, inhibits the formation of a polymer from those monomers during the induction time. After the induction time has lapsed, the polymer's formation occurs at substantially the same rate that it would form at in the absence of the polymerization inhibitor.

A "polymerization retarder" does not exhibit an induction time, but instead once added to a polymerizable monomer composition reduces the rate at which the formation of the polymer occurs relative to the rate at which it would have formed in the absence of the composition of matter.

Polymerization inhibitors, as opposed to polymerization retarders, are generally consumed rapidly. Polymerization retarders, while they slow down the rate of polymerization reactions, are not as effective as polymerization inhibitors. Polymerization retarders, however, are usually not consumed as quickly as polymerization inhibitors.

Polymerization inhibitors and polymerization retarders can be considered generally as "antipolymerants" which are compounds that can inhibit or reduce the formation of polymers from one or more radically polymerizable compounds.

A "stabilizer" refers to a compound that can provide an improvement with regards to the functionality of the polymerization inhibitor and retarder when used in combination (as compared to a composition that does not include the stabilizer). Without being bound by a particular theory or mechanism of stabilizer action, the stabilizer may reduce an antagonistic effect that a polymerization inhibitor and retarder have towards each other when combined, or enhance the functionality of either or both the polymerization inhibitor and/or retarder. For example, the stabilizer may enhance the ability of the inhibitor and/or retarder to inhibit and/or retard polymerization, respectively, or may enhance the functional life of the inhibitor and/or retarder, and thereby extend the induction time of an inhibitor, etc. Alternatively, the amine stabilizer may be referred to as an "enhancer" or "additive" or simply an "amine compound" for a polymerization inhibitor and retarder-containing composition.

Aspects of the disclosure provide a composition for inhibiting monomer polymerization that include an inhibitor compound that has an N-to-O functional group, a retarder compound that is a quinone methide; and an amine stabilizer compound that has a primary or secondary amine group. A composition that includes these components (and any one or more optional component) can be in a desired form, such as in a liquid form, a dry form, or as a suspension or dispersion. The inhibitor, retarder, and amine stabilizer can be in desired physical states in the composition, such as in a dissolved state, in a partially dissolved state, in a suspended state, or in a dry mixture. Also, the inhibitor, retarder, and amine stabilizer can be in desired forms in the composition, such as optionally in particulate forms. If one or more of the components is in a particulate form, the particles can optionally be described in terms of particle size (e.g., particles of a size range) and/or shape. The form of the composition and the state of the components therein can be chosen by selection of inhibitor, retarder, and stabilizer compound, with an understanding of the physical property of each compound. The form of the composition and the state of the components therein can also be affected by the inclusion of one or more optional components, such as a solvent, or solvent mixture, or other excipient compounds like surfactants, dispersants, etc. The form of the composition and the state of the components therein can also be affected by temperature, and composition properties may optionally be described in circumstances at a particular temperature (e.g., at a storage temperature such as 5° C. or below, at room temperature (25° C.), or at a temperature used for monomer synthesis and/or processing (e.g., about 100° C. or greater, about 150° C., about 175° C., etc.).

A composition including the inhibitor, retarder, and stabilizer compound can optionally include other components in the composition (e.g., described in terms of a composition "comprising" the inhibitor, retarder, and stabilizer). For example, such compositions can include other components such as a solvent, surfactants, dispersants, etc. If an optional component is present in the composition it may be described in terms of a weight amount relative to one or more of the inhibitor, retarder, and stabilizer compounds in the composition. The optional component may be present in a weight amount greater than, or an amount less than, any one of the inhibitor, retarder, or stabilizer, or the total amount of inhibitor, retarder, and stabilizer.

As used herein, the term "optional" or "optionally" means that the subsequently described object (e.g., compound), event (e.g., processing step), or circumstance may, but need not occur, and that the description includes instances where the object, event, or circumstance occurs and instances in which it does not.

Compositions of the disclosure can include those recited compounds and optionally can include other components in the composition but in very small amounts (e.g., described in terms of a composition "consisting essentially of" the recited components). For example, such compositions can include one or more other components but not in an amount that is greater than about 1% (wt), about 0.5% (wt), or about 0.1% (wt), of the total composition. A composition that consists essentially of the inhibitor, retarder, stabilizer, and a solvent can optionally include one or more other components but in an amount less than about 1% (wt) of the total composition. In a composition "consisting of" the recited components there is no other measurable amount of component other than the recited component.

Likewise, the chemistries of compounds of the disclosure, including the amine stabilizer, polymerization inhibitor, and polymerization retarder can, in some embodiments, be described in terms of the compound "consisting of" certain atoms or certain chemical groups. For example, a compound consisting of carbon (C), hydrogen (H), and nitrogen (N) will not have any other types of atoms aside from C, H, and N. As another example, a compound consisting of a hydrocarbyl group and a primary amine group will not have any other chemical groups aside from these.

As used herein, the terms "substantially" and "consisting essentially of" modifying, for example, the type or quantity of an ingredient in a composition, a property, a measurable quantity, a method, a position, a value, or a range, employed in describing the embodiments of the disclosure, refers to a variation that does not affect the overall recited composition, property, quantity, method, position, value, or range thereof in a manner that negates an intended composition, property, quantity, method, position, value, or range. Examples of intended properties include, solely by way of nonlimiting examples thereof, dispersibility, stability, rate, solubility, and the like; intended values include weight of a component added, concentration of components added, and the like. The effect on methods that are modified include the effects caused by variations in type or amount of materials used in a process, variability in machine settings, the effects of ambient conditions on a process, and the like wherein the manner or degree of the effect does not negate one or more intended properties or results; and like proximate considerations. Where modified by the term "substantially" or "consisting essentially of," the claims appended hereto include equivalents to these types and amounts of materials.

As used herein, the term "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. Further, where "about" is employed to describe any range of values, for example "about 1 to 5" the recitation means "1 to 5" and "about 1 to about 5" and "1 to about 5" and "about 1 to 5" unless specifically limited by context.

Some R groups in formulas of the disclosure can include hydrocarbon-containing groups such as alkyl groups, including linear, branched, and cyclic alkyl groups, aryl groups, alkyl aryl groups (e.g., phenyl-propyl), aryl alkyl groups (e.g., propyl-phenyl), and combinations thereof. Cyclic alkyl or aryl groups can have fused structures such as decahydronaphthalene, naphthalene, tetradecahydro-anthracene, anthracene, etc. In some embodiments, these hydrocarbon groups can be defined by the number of carbon atoms in the group, such as 1-22 carbons, 1-18 carbons, 1-15 carbons, 1-12 carbons, 1-9 carbons, or 1-6 carbons. Compositions and methods of the disclosure include or use a polymerization inhibitor that includes an N-to-O bond. In use, the polymerization inhibitor can generate a stable free radical on the oxygen atom. Exemplary polymerization inhibitors that have an N-to-O bond include nitroxide-, amine oxide-, hydroxylamine-, nitro-, nitroso-, and nitrone-containing compounds.

In some embodiments, the polymerization inhibitor is a nitroxide- or hydroxylamine-containing compound. In methods of the disclosure, nitroxide radicals can trap propagating monomer radicals in thermally unstable species and inhibit polymerization. A nitroxide group, which can also be referred to as an amine-N-oxide group, is a functional group including an NO bond and side groups attaching to the nitrogen. Nitroxide (nitroxyl) radicals are oxygen-centered radicals with the free electron delocalized over the N—O bond. Nitroxide-containing polymerization inhibitors can include N—O resonance structures that contribute to the stability of nitroxide radicals.

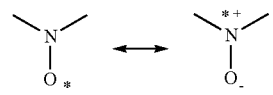

Nitroxide-containing polymerization inhibitors can have substantial life time which allows them to be used as persistent free radicals. Nitroxide and hydroxylamine compounds can include the following chemistry:

wherein X is an unpaired electron or H.

Exemplary nitroxide-containing polymerization inhibitors include compounds of Formula I and II:

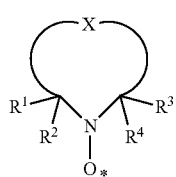

Formula I

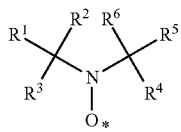

Formula II wherein $R^1$, $R^2$, $R^3$, and $R^4$, (Formula I) and $R^2$, $R^3$, $R^4$, $R^5$, and $R^6$, (Formula II) are independently selected from H, linear, branched, cyclic alkyl, and aryl, and in Formula I, X is a divalent group of two or three atoms, which completes the ring structure. In preferred aspects, in Formula I, $R^1$, $R^2$, $R^3$, and $R^4$, are independently selected from H, linear, branched, and cyclic C1-C6 alkyl, and X is a divalent group of two or three atoms selected from the group consisting of C, N, and O, wherein at least one atom is C. In preferred aspects, in Formula II, $R^1$, $R^2$, $R^3$, $R^4$, $R^5$, and $R^6$ are independently selected from H, linear, branched, and cyclic C1-C6 alkyl.

An exemplary nitroxide-containing inhibitor of Formula II is di-tert-butyl nitroxyl.

In preferred embodiments, exemplary nitroxide-containing polymerization inhibitors include compounds of formula III:

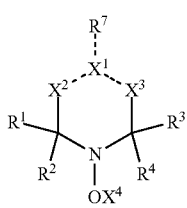

Formula III wherein $R^1$, $R^2$, $R^3$, and $R^4$ are independently selected from H, C1-C22 linear, branched, cyclic alkyl, and aryl, wherein $X^1 \ldots X^2$ and $X^1 \ldots X^3$ is C—C or C=C, wherein $X^4$ is H or an unpaired electron, and wherein $X^1 \ldots R^7$ is selected from C—O, C=O, C—H, C—$OR^8$, and C—$OC(O)R^8$, and wherein $R^8$ is selected from H, and C1-C22 linear, branched, and cyclic alkyl, aryl, aryl alkyl, and alkyl aryl.

Exemplary nitroxide-containing polymerization inhibitor include, but are not limited to: 2,2,6,6-tetramethylpiperidinyl-1-oxyl (TEMPO), 4-hydroxy-2,2,6,6-tetramethylpiperidinyl-1-oxyl(HTMPO), 4-oxo-2,2,6,6-tetramethylpiperidinyl-1-oxyl (OTEMPO), di-tert-butyl nitroxyl, 1-oxyl-2,2,6,6-tetramethyl-4-n-propoxypiperidine, 1-oxyl-2,2,6,6-tetramethyl-4-n-butoxypiperidine, 1-oxyl-2,2,6,6-tetramethyl-4-t-butoxypiperidine, 1-oxyl-2,2,6,6-tetramethyl-4-s-butoxypiperidine, 1-oxyl-2,2,6,6-tetramethyl-4-(2-methoxyethoxy)piperidine, 1-oxyl-2,2,6,6-tetramethyl-4-(2-methoxyethoxyacetoxy)piperidine, 1-oxyl-2,2,6,6-tetramethylpiperidin-4-yl stearate, 1-oxyl-2,2,6,6-tetramethylpiperidin-4-yl acetate, 1-oxyl-2,2,6,6-tetramethylpiperidin-4-yl butyrate, 1-oxyl-2,2,6,6-tetramethylpiperidin-4-yl 2-ethylhexanoate, 1-oxyl-2,2,6,6-tetramethylpiperidin-4-yl octanoate, 1-oxyl-2,2,6,6-tetramethylpiperidin-4-yl laurate, 1-oxyl-2,2,6,6-tetramethylpiperidin-4-yl benzoate, 1-oxyl-2,2,6,6-tetramethylpiperidin-4-yl 4-tert-butylbenzoate, 1-oxyl-2,2,6,6-tetramethyl-4-allyloxy-piperidine, 1-oxyl-2,2,6,6-tetramethyl-4-acetamidopiperidine, 1-oxyl-2,2,6,6-tetramethyl-4-(N-butylformamido)piperidine, N-(1-oxyl-2,2,6,6-tetramethylpiperidin-4-yl)-caprolactam, N-(1-oxyl-2,2,6,6-tetramethylpiperidin-4-yl)-dodecylsuccinimide, 1-oxyl-2,2,6,6-tetramethyl-4-(2,3-dihydroxypropoxy)piperidine, 1-oxyl-2,2,6,6-tetramethyl-4-(2-hydroxyl-4-oxapentoxy)piperidine, and mixtures thereof. (See, for example, U.S. Pat. No. 9,266,797.)

Other exemplary nitroxide-containing polymerization inhibitors include two or three nitroxyl groups. Such compounds may be bis- or tris-compounds derived from compounds of Formula I. For example, nitroxide-containing ring structures can be linked by a divalent linking group $Q^1$ to provide bis-nitroxide compounds according to formula IV, or a trivalent linking group $Q^2$ to provide a tris-nitroxide compounds according to formula V, wherein $R^{1'}$, $R^{2'}$, $R^{3'}$, and $R^{4'}$, and $R^{1''}$, $R^{2''}$, $R^{3''}$, and $R^{4''}$, have the same definitions as $R^1$, $R^2$, $R^3$, and $R^4$, respectively, and X' and X'', have the same definitions as X, as described herein. $Q^1$ can be a divalent linking group formed from a compound selected from the group consisting of diacids, diesters, diamides, diols, diamines, preferably having 1-22 carbons, 1-18 carbons, 1-15 carbons, 1-12 carbons, 1-9 carbons, or 1-6 carbons, and $Q^2$ can be a trivalent linking group formed from a compound selected from the group consisting of triacids, triols, amines, and triazines preferably having 1-22 carbons, 1-18 carbons, 1-15 carbons, 1-12 carbons, 1-9 carbons, or 1-6 carbons.

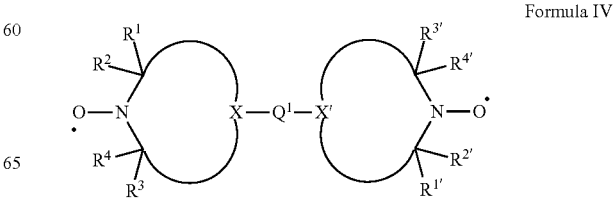

Formula IV

-continued

Formula V

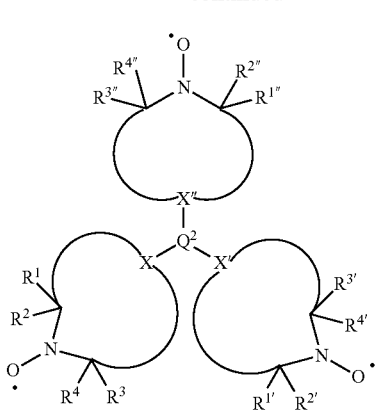

Exemplary bis-nitroxide and tris-nitroxide polymerization inhibitor compound include bis(1-oxyl-2,2,6,6-tetramethylpiperidin-4-yl) succinate, bis(1-oxyl-2,2,6,6-tetramethylpiperidin-4-yl) adipate, bis(1-oxyl-2,2,6,6-tetramethylpiperidin-4-yl) sebacate, bis(1-oxyl-2,2,6,6-tetramethylpiperidin-4-yl) n-butylmalonate, bis(1-oxyl-2,2,6,6-tetramethylpiperidin-4-yl) phthalate, bis(1-oxyl-2,2,6,6-tetramethylpiperidin-4-yl) isophthalate, bis(1-oxyl-2,2,6,6-tetramethylpiperidin-4-yl) terephthalate, bis(1-oxyl-2,2,6,6-tetramethylpiperidin-4-yl) hexahydroterephthalate, N,N'-bis(1-oxyl-2,2,6,6-tetramethylpiperidin-4-yl) adipamide, 2,4,6-tris-[N-butyl-N-(1-oxyl-2,266-tetramethylpiperidin-4-yl)]-s-triazine, 2,4,6-tris-[N-(1-oxyl-2,2,6,6-tetramethylpiperidin-4-yl)]-s-triazine, 4,4'-ethylenebis(1-oxyl-2,2,6,6-tetramethylpiperazin-3-one), and mixtures thereof. (See, for example, U.S. Pat. No. 9,266,797.)

In some embodiments, hydroxylamine polymerization inhibitors of formula XIII are used:

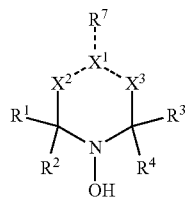

wherein $R^1$, $R^2$, $R^3$, $R^4$, $R^7$ $X^1$, $X^2$, $X^3$ have the same meanings as described in Formula III.

The inhibitor compound can be a nitroxide-containing compound having a piperidonoxyl group of formula XIV:

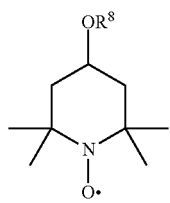

wherein $R^8$ is selected from H, C1-C22 alkyl, C1-C22 aryl, C1-C22 aryl alkyl, and C1-C22 alkyl aryls. Exemplary compounds of formula XIV include 4-methoxy-2,2,6,6-tetramethylpiperidin-1-oxy, 4-ethoxy-2,2,6,6-tetramethylpiperidin-1-oxy, 4-propoxy-2,2,6,6-tetramethylpiperidin-1-oxy, 4-butoxy-2,2,6,6-tetramethylpiperidin-1-oxy, 4-pentoxy-2,2,6,6-tetramethylpiperidin-1-oxy, 4-hexyloxy-2,2,6,6-tetramethylpiperidin-1-oxy, 4-heptyloxy-2,2,6,6-tetramethylpiperidin-1-oxy, 4-octyloxy-2,2,6,6-tetramethylpiperidin-1-oxy, 4-nonyloxy-2,2,6,6-tetramethylpiperidin-1-oxy, 4-decyloxy-2,2,6,6-tetramethylpiperidin-1-oxy, 4-undecyloxy-2,2,6,6-tetramethylpiperidin-1-oxy, 4-dodecyloxy-2,2,6,6-tetramethylpiperidin-1-oxy, 4-tridecyloxy-2,2,6,6-tetramethylpiperidin-1-oxy, 4-tetradecyloxy-2,2,6,6-tetramethylpiperidin-1-oxy, 4-pentadecyloxy-2,2,6,6-tetramethylpiperidin-1-oxy, 4-hexadecyloxy-2,2,6,6-tetramethylpiperidin-1-oxy, 4-heptadecyloxy-2,2,6,6-tetramethylpiperidin-1-oxy, 4-octadecyloxy-2,2,6,6-tetramethylpiperidin-1-oxy, 4-nodecyloxy-2,2,6,6-tetramethylpiperidin-1-oxy, 4-decyloxy-2,2,6,6-tetramethylpiperidin-1-oxy, 4-icosyloxy-2,2,6,6-tetramethylpiperidin-1-oxy, 4-henicosyloxy-2,2,6,6-tetramethylpiperidin-1-oxy, 4-docosyloxy-2,2,6,6-tetramethylpiperidin-1-oxy, 4-(phenoxy)-2,2,6,6-tetramethylpiperidin-1-oxy, 4-(benzyloxy)-2,2,6,6-tetramethylpiperidin-1-oxy, and 2,2,6,6-tetramethyl-4-(naphthalen-2-yloxy)piperidin-1-oxy.

Other nitroxide-containing inhibitor compounds having a piperidonoxyl group can be bis-based compounds such as 4,4'-(ethane-1,2-diylbis(oxy))bis(2,2,6,6-tetramethylpiperidin-1-oxy), 4,4'-(propane-1,2-diylbis(oxy))bis(2,2,6,6-tetramethylpiperidin-1-oxy), 4,4'-(butane-1,4-diylbis(oxy))bis(2,2,6,6-tetramethylpiperidin-1-oxy), and can be tris-based compounds such as 4,4',4''-(propane-1,2,3-triyltris(oxy))tris(2,2,6,6-tetramethylpiperidin-1-oxy). The inhibitor compound can be a nitroxide-containing compound having a piperidinol group according to formula XV:

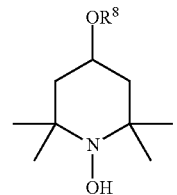

wherein $R^8$ is selected from H, and C1-C22 alkyl, C1-C22 aryl, C1-C22 aryl alkyl, and C1-C22 alkyl aryl. Exemplary compounds of formula XV include 2,2,6,6-tetramethylpiperin-1,4-diol, 4-methoxy-2,2,6,6-tetramethylpiperidin-1-ol, 4-ethoxy-2,2,6,6-tetramethylpiperidin-1-ol, 4-propoxy-2,2,6,6-tetramethylpiperidin-1-ol, 4-butoxy-2,2,6,6-tetramethylpiperidin-1-ol, 4-pentoxy-2,2,6,6-tetramethylpiperidin-1-ol, 4-hexyloxy-2,2,6,6-tetramethylpiperidin-1-ol, 4-heptyloxy-2,2,6,6-tetramethylpiperidin-1-ol, 4-octyloxy-2,2,6,6-tetramethylpiperidin-1-ol, 4-nonyloxy-2,2,6,6-tetramethylpiperidin-1-ol, 4-decyloxy-2,2,6,6-tetramethylpiperidin-1-ol, 4-undecyloxy-2,2,6,6-tetramethylpiperidin-1-ol, 4-dodecyloxy-2,2,6,6-tetramethylpiperidin-1-ol, 4-tridecyloxy-2,2,6,6-tetramethylpiperidin-1-ol, 4-tetradecyloxy-2,2,6,6-tetramethylpiperidin-1-ol, 4-pentadecyloxy-2,2,6,6-tetramethylpiperidin-1-ol, 4-hexadecyloxy-2,2,6,6-tetramethylpiperidin-1-ol, 4-heptadecyloxy-2,2,6,6-tetramethylpiperidin-1-ol, 4-octadecyloxy-2,2,6,6-tetramethylpiperidin-1-ol, 4-nodecyloxy-2,2,6,6-tetramethylpiperidin-1-ol, 4-decyloxy-2,2,6,6-tetramethylpiperidin-1-ol, 4-icosyloxy-2,2,6,6-tetramethylpiperidin-1-ol, 4-henicosyloxy-2,2,6,6-tetramethylpiperidin-1-ol, 4-docosyloxy-2,2,6,6-tetramethylpiperidin-1-ol, 4-(phenoxy)-2,2,6,6- tetramethylpiperidin-1-ol, 4-(benzyloxy)-2,2,6,6-tetramethylpiperidin-1-ol, and 2,2,6,6-tetramethyl-4-(naphthalen-2-yloxy)piperidin-1-ol.

Other nitroxide-containing inhibitor compounds having a piperidinol group can be bis-based compounds such as 4,4'-(ethane-1,2-diylbis(oxy))bis(2,2,6,6-tetramethylpiperidin-1-ol), 4,4'-(propane-1,2-diylbis(oxy))bis(2,2,6,6-tetramethylpiperidin-1-ol), 4,4'-(butane-1,4-diylbis(oxy))bis(2,2,6,6-tetramethylpiperidin-1-ol), and can be tris-based compounds such as 4,4',4''-(propane-1,2,3-triyltris(oxy))tris (2,2,6,6-tetramethylpiperidin-1-ol).

The inhibitor compound can be a nitroxide-containing compound having a piperidinoxy group according to formula XVI:

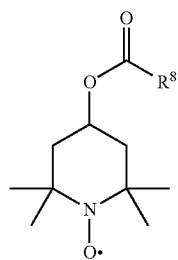

wherein $R^8$ is selected from H, and C1-C22 alkyl, C1-C22 aryl, C1-C22 aryl alkyl, and C1-C22 alkyl aryl. Exemplary compounds of formula XVI include 1-oxyl-2,2,6,6-tetramethylpiperidin-4-yl acetate, 1-oxyl-2,2,6,6-tetramethylpiperidin-4-yl propanoate, 1-oxyl-2,2,6,6-tetramethylpiperidin-4-yl butyrate, 1-oxyl-2,2,6,6-tetramethylpiperidin-4-yl pentanoate, 1-oxyl-2,2,6,6-tetramethylpiperidin-4-yl hexanoate, 1-oxyl-2,2,6,6-tetramethylpiperidin-4-yl heptanoate, 1-oxyl-2,2,6,6-tetramethylpiperidin-4-yl octanoate, 1-oxyl-2,2,6,6-tetramethylpiperidin-4-yl nonanoate, 1-oxyl-2,2,6,6-tetramethylpiperidin-4-yl decanoate, 1-oxyl-2,2,6,6-tetramethylpiperidin-4-yl undecanoate, 1-oxyl-2,2,6,6-tetramethylpiperidin-4-yl dodecanoate, 1-oxyl-2,2,6,6-tetramethylpiperidin-4-yl 2-ethylhexanoate, 1-oxyl-2,2,6,6-tetramethylpiperidin-4-yl stearate, 1-oxyl-2,2,6,6-tetramethylpiperidin-4-yl benzoate, 1-oxyl-2,2,6,6-tetramethylpiperidin-4-yl palmitoate, 1-oxyl-2,2,6,6-tetramethylpiperidin-4-yl behenoate, and 1-oxyl-2,2,6,6-tetramethylpiperidin-4-yl 4-tert-butylbenzoate.

Other nitroxide-containing inhibitor compounds having a piperidinoxy group can be bis-based compounds such as bis(1-oxyl-2,2,6,6-tetramethylpiperidin-4-yl) succinate, bis (1-oxyl-2,2,6,6-tetramethylpiperidin-4-yl) adipate, bis(1-oxyl-2,2,6,6-tetramethylpiperidin-4-yl) oxalate, bis(1-oxyl-2,2,6,6-tetramethylpiperidin-4-yl) malonate, bis(1-oxyl-2,2,6,6-tetramethylpiperidin-4-yl) fumarate, bis(1-oxyl-2,2,6,6-tetramethylpiperidin-4-yl) sebacate, bis(1-oxyl-2,2,6,6-tetramethylpiperidin-4-yl) n-butylmalonate, bis(1-oxyl-2,2,6,6-tetramethylpiperidin-4-yl) phthalate, bis(1-oxyl-2,2,6,6-tetramethylpiperidin-4-yl) isophthalate, bis(1-oxyl-2,2,6,6-tetramethylpiperidin-4-yl) terephthalate, bis(1-oxyl-2,2,6,6-tetramethylpiperidin-4-yl) hexahydroterephthalate, and N,N'-bis(1-oxyl-2,2,6,6-tetramethylpiperidin-4-yl)adipamide, and 4,4'-ethylenebis(1-oxyl-2,2,6,6-tetramethylpiperazin-3-one), and can be tris-based compounds such as 2,4,6-tris-[N-butyl-N-(1-oxyl-2,2,6,6-tetramethylpiperidin-4-yl]-s-triazine and 4,4',4''-(propane-1,2,3-triyltris(oxy))tris (2,2,6,6-tetramethylpiperidin-1-ol). Yet other nitroxide-containing inhibitor compounds having a piperidinoxy group can be N-(1-oxyl-2,2,6,6-tetramethylpiperidin-4-yl)-caprolactam and N-(1-oxyl-2,2,6,6-tetramethylpiperidin-4-yl)-dodecylsuccinimide.

The inhibitor compound can be a nitroxide-containing compound having a piperidinol group according to formula XVII:

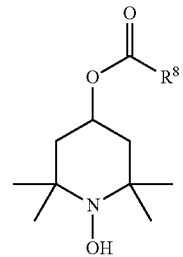

wherein $R^8$ is selected from H, and C1-C22 alkyls, aryls, aryl alkyls, and alkyl aryls. Exemplary compounds of formula XVII include 1-hydroxy-2,2,6,6-tetramethylpiperidin-4-yl acetate, 1-hydroxy-2,2,6,6-tetramethylpiperidin-4-yl propanoate, 1-hydroxy-2,2,6,6-tetramethylpiperidin-4-yl butyrate, 1-hydroxy-2,2,6,6-tetramethylpiperidin-4-yl pentanoate, 1-hydroxy-2,2,6,6-tetramethylpiperidin-4-yl hexanoate, 1-hydroxy-2,2,6,6-tetramethylpiperidin-4-yl heptanoate, 1-hydroxy-2,2,6,6-tetramethylpiperidin-4-yl octanoate, 1-hydroxy-2,2,6,6-tetramethylpiperidin-4-yl nonanoate, 1-hydroxy-2,2,6,6-tetramethylpiperidin-4-yl decanoate, 1-hydroxy-2,2,6,6-tetramethylpiperidin-4-yl undecanoate, 1-hydroxy-2,2,6,6-tetramethylpiperidin-4-yl dodecanoate, 1-hydroxy-2,2,6,6-tetramethylpiperidin-4-yl 2-ethylhexanoate, 1-hydroxy-2,2,6,6-tetramethylpiperidin-4-yl stearate, 1-hydroxy-2,2,6,6-tetramethylpiperidin-4-yl benzoate, 1-hydroxy-2,2,6,6-tetramethylpiperidin-4-yl palmitoate, 1-hydroxy-2,2,6,6-tetramethylpiperidin-4-yl behenoate, and 1-hydroxy-2,2,6,6-tetramethylpiperidin-4-yl 4-tert-butylbenzoate.

Other nitroxide-containing inhibitor compounds having a piperidinol group can be bis-based compounds such as bis(1-hydroxy-2,2,6,6-tetramethylpiperidin-4-yl) succinate, bis(1-hydroxy-2,2,6,6-tetramethylpiperidin-4-yl) adipate, bis(1-hydroxy-2,2,6,6-tetramethylpiperidin-4-yl) sebacate, bis(1-hydroxy-2,2,6,6-tetramethylpiperidin-4-yl) n-butylmalonate, bis(1-hydroxy-2,2,6,6-tetramethylpiperidin-4-yl) phthalate, bis(1-hydroxy-2,2,6,6-tetramethylpiperidin-4-yl) isophthalate, bis(1-hydroxy-2,2,6,6-tetramethylpiperidin-4-yl) terephthalate, bis(1-hydroxy-2,2,6,6-tetramethylpiperidin-4-yl) hexahydroterephthalate, N,N'-bis(1-hydroxy-2,2,6,6-tetramethylpiperidin-4-yl)adipamide, and 4,4'-ethylenebis(1-hydroxy-2,2,6,6-tetramethylpiperazin-3-one), and can be tris-based compounds such as 2,4,6-tris-[N-butyl-N-(1-hydroxy-2,2,6,6-tetramethylpiperidin-4-yl]-s-triazine, Yet other nitroxide-containing inhibitor compounds having a piperidinol group can be N-(1-hydroxy-2,2,6,6-tetramethylpiperidin-4-yl)-caprolactam and N-(1-hydroxy-2,2,6,6-tetramethylpiperidin-4-yl)-dodecylsuccinimide Exemplary hydroxylamine-containing polymerization inhibitors include, but are not limited to: 1-hydroxy-2,2,6,6-tetramethylpiperidine (TEMPOH), 1,4-dihydroxy-2,2,6,6-tetramethylpiperidine (HTMPOH), and 1-hydroxy-4-oxo-2,2,6,6-tetramethylpiperidine (OTEMPOH), N,N-diethylhydroxylamine, and N-isopropylhydroxylamine.

Exemplary nitro-containing polymerization inhibitors include, but are not limited to: nitrobenzene, nitrophenol, dinitrophenol, 2,4-dinitro-6-s-butylphenol, 2,4-dinitro-o-cresol, and diphenyl picrylhydrazyl.

Exemplary nitroso-containing polymerization inhibitors include, but are not limited to: nitrosobenzene, nitrosophenol, dinitrosophenol, dinitrosotoluene, nitrosophenylhydroxylamine.

Compositions and methods of the disclosure include or use a polymerization retarder that has a quinone methide chemistry.

In some embodiments, the quinone methide retarder is a compound of Formula VI:

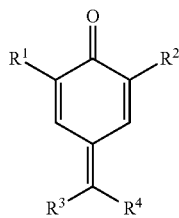

wherein $R^1$ and $R^2$ are independently selected from C4-C18 alkyl, C5-C12 cycloalkyl, phenyl, and C7-C15 cycloalkyl, wherein $R^3$ and $R^4$ are independently selected from —H, C1-C18 alkyl, phenyl, substituted phenyl, C5-C12 cycloalkyl, —CN, —COOH, —C=$CR^5$, —C≡$CR^5$, —$COOR^5$, —$COR^5$, —$OCOR^5$, —$CONR^5$, wherein $R^5$ is selected from H, C1-C18 alkyl, C5-C12 cycloalkyl, phenyl, and C7-C15 cycloalkyl, and substituted phenyl. In preferred embodiments, $R^1$ and $R^2$ are independently selected from C4-C18 alkyl, and preferably C4-C6 linear or brached alkyl, such as tert-butyl.

Exemplary the quinone methide retarders include, 2,6-di-tert-butyl-4-benzylidene-cyclohexa-2,5-dienone, 2,6-di-tert-butyl-4-(4-nitrobenzylidene)-cyclohexa-2,5-dienone, 2,6-di-tert-butyl-3-(4-nitrobenzylidene)-cyclohexa-2,5-dienone, 2,6-di-tert-butyl-4-(4-cyanobenzylidene)-cyclohexa-2,5-dienone, 2,6-di-tert-butyl-4-(4-methoxybenzylidene)-cyclohexa-2,5-dienone and 2,6-di-tert-butyl-4-(3,5-di-tert-butyl-4-hydroxybenzylidene)-cyclohexa-2,5-dienone. See, for example, U.S. Pat. No. 5,616,774 and U.S. App. Pub. No. 2006/0163539.

Compositions and methods of the disclosure include or use a compound that has a primary or secondary amine group (herein referred to as the "amine stabilizer") and that is different than the N—O group containing polymerization inhibitor and the quinone methide retarder. The amine stabilizer, when used in combination with the N—O group containing polymerization inhibitor and the quinone methide retarder, can improve performance of the inhibitor and retarder. For example, the amine stabilizer can inhibit polymerization of a monomer composition as compared to use of the inhibitor alone, the retarder alone, or a mixture of the inhibitor and retarder.

The amine stabilizer has one or more primary amine groups, one or more secondary amine groups, or a combination of primary and secondary amine groups. In embodiments, amine stabilizer may exclude certain chemistries, such as tertiary amine groups, ethylenically unsaturated groups, N—O groups, or combinations thereof. Accordingly, in some embodiments, the amine stabilizer consists of the atoms of carbon (C), hydrogen (H), and nitrogen (N). Accordingly, in some embodiments, the amine stabilizer consists of (a) a hydrocarbyl group (a univalent radical derived from a hydrocarbon, such as methyl, ethyl, etc.), a hydrocarbylene group (a divalent radical derived from a hydrocarbon, such as ethylene, propylene, etc.), or both hydrocarbyl and hydrocarbylene groups, and (b) one or more primary amine group(s), one or more secondary amine groups, or both primary and secondary amine groups.

The amine stabilizer can also be described in terms of atomic composition, for example, amine stabilizer has one or more primary and/or secondary amine groups, and at least 4 carbon atoms. In some preferred embodiments, the amine stabilizer has a number of carbons in the range of 6-24, in the range of 7-24, or in the range of 8-24. The amine stabilizer can optionally include one or more heteroatoms, such as oxygen or sulfur.

Carbons in the amine stabilizer can be described in terms of carbon-containing groups, and in some embodiments the stabilizer includes at least one linear, branched, or cyclic alkyl group (i.e., hydrocarbyl). In some cases, the amine stabilizer has a single alkyl group, with the total number of carbon atoms, such as 4 or more (e.g., 6-24) being present in the single alkyl group. In other cases, the amine stabilizer has more than one alkyl group, with the total number of carbon atoms, such as 4 or more (e.g., 6-24) being divided up into the multiple alkyl groups. In some embodiments, the carbon-containing groups of the amine stabilizer do not include any: ethylenic unsaturation (i.e., C=C bonds); does not include any tertiary amine groups; does not include any quaternary amine groups; or combinations thereof.

In some embodiments, the amine stabilizer can be a compound of formula VII: $R^1NH_2$. In formula VII, $R^1$ is a linear, branched, or cyclic alkyl group of at least 4 carbon atoms, such as a number of carbon atoms in the range of 4-24, 6-24, or 8-24. Exemplary compounds include:

4 carbon primary amines such as n-butylamine, sec-butyamine, tert-butylamine, isobutylamine, 5 carbon primary amines such as 2-methyl-2-butanamine, 2-methylbutylamine, 3-methylbutan-2-amine, 3-methylbutylamine, n-pentylamine;

6 carbon primary amines such as n-hexylamine, 3,3-dimethyl-2-butanamine, isohexylamine, 3-(aminomethyl)pentane, 3,3-dimethylbutan-2-amine, 3,3-dimethylbutan-2-amine, 4-methylpentan-2-amine, 3,3-dimethylbutan-1-amine, 3-methylpentan-2-amine, hexan-2-amine, 4-methylpentan-1-amine, 2-methylpentan-1-amine, 3-methylpentan-2-amine, 2,3-dimethylbutan-1-amine, 2-methylpentan-2-amine, 3-methylpentan-3-amine, 2,3-dimethylbutan-2-amine, hexan-3-amine, aminocyclohexane, and the like;

7 carbon primary amines such as heptan-1-amine, heptan-2-amine, heptan-3-amine, heptan-4-amine, 5-methyhexan-2-amine, 4-methylhexan-2-amine, 3-ethylpentan-1-amine, 3-methylhexan-1-amine, 2,4-dimethylpentan-3-amine, 3-ethylpentan-3-amine, 2,4-dimethylpentan-2-amine, 2,3,3-trimethylbutan-2-amine, 3,4-dimethylpentan-2-amine, 5-methylhexan-1-amine, 4-methylhexan-3-amine, 3-methylhexan-2-amine, 3-ethylpentan-2-amine, 2,3-dimethylpentan-3-amine, 3-methylhexan-3-amine, 5-methylhexan-3-amine, 2,4-dimethylpentan-1-amine, 2,3,3-trimethylbutan-1-amine, 2-methylhexan-1-amine, 3-(aminomethyl)hexane, 2-methylhexan-2-amine, 2,2-dimethylpentan-3-amine, 2-methylhexan-3-amine, 2,2-dimethylpentan-1-amine, 4-methylhexan-1-amine, 4,4-dimethylpentan-1-amine, 3,4-dimethylpentan-1-amine, 2,3-dimethylpentan-1-amine, 2,3-dimethylpentan-2-amine, 4,4-dimethylpentan-2-amine, 2,2,3-trimethylbutan-1-amine, and 3,3-dimethylpentan-1-amine, cycloheptanamine, 2-methylcyclohexan-1-amine, 1-cyclohexylmethanamine, 1-methylcyclohexan-1-amine, 4-methylcyclohexan-1-amine, 3-methylcyclohexan-1-amine, and the like;

8 carbon primary amines such as n-octylamine, octan-2-amine, 6-methylheptan-2-amine, 3-(aminomethyl)heptane, 4,4-trimethylpentan-2-amine, octan-2-amine, 6-methylheptan-2-amine, 6-methylheptan-1-amine, 2-methylheptan-2-amine, 4-methylheptan-3-amine, 3,5-dimethylhexan-1-amine, 3-ethyl-4-methylpentan-1-amine, 4-ethylhexan-1-amine, 2,5-dimethylhexan-2-amine, 3,5-dimethylhexan-2-amine, 3-methylheptan-2-amine, 3-ethylhexan-2-amine, 3,5-dimethylhexan-3-amine, 3-ethyl-2-methylpentan-3-amine, 3-ethylhexan-3-amine, 2,3,4-trimethylpentan-3-amine, 2,3-dimethylhexan-3-amine, 2,5-dimethylhexan-3-amine, 2-methylheptan-4-amine, 2,2,4-trimethylpentan-3-amine, 4-(aminomethyl)heptane, 2,5-dimethylhexan-1-amine, 4-methylheptan-1-amine, 2-methylheptan-1-amine, 2,4-dimethylhexan-1-amine, 4-(aminomethyl)-2-methylhexane, 3-(aminomethyl)-2-methylhexane, octan-4-amine, 2,2-dimethylhexan-3-amine, octan-3-amine, 6-methylheptan-3-amine, 2-methylheptan-3-amine, 2,2-dimethylhexan-1-amine, 2,2-dimethylhexan-3-amine, 2,2,4-trimethylpentan-1-amine, 3-(aminomethyl)-3-methylhexane, 3-(aminomethyl)-3-ethylpentane, 4-ethylhexan-2-amine, 5-methylheptan-2-amine, 2,4-dimethylhexan-2-amine, 3-methylheptan-3-amine, 4-methylheptan-2-amine, 5,5-dimethylhexan-2-amine, 5,5-dimethylhexan-1-amine, 3,4-dimethylhexan-1-amine, 3-ethyl-4-methylpentan-2-amine, 3,4-dimethylhexan-3-amine, 6-methylheptan-2-amine, 3-(aminomethyl)heptane, octan-2-amine, 5-methylheptan-3-amine, 2,4-dimethylhexan-3-amine, 3-methylheptan-4-amine, 3,4,4-trimethylpentan-1-amine, 5-dimethylhexan-3-amine, 2,4,4-trimethylpentan-1-amine, 5-methylheptan-1-amine, 4-methylheptan-4-amine, 4,5-dimethylhexan-2-amine, 4,4-dimethylhexan-2-amine, 4,5-dimethylhexan-3-amine, 3-(aminomethyl)-2,4-dimethylpentane, 3-ethyl-2-methylpentan-1-amine, 2,3,4-trimethylpentan-2-amine, 2,3,4-trimethylpentan-1-amine, 4,5-dimethylhexan-1-amine, 3-methylheptan-1-amine, 3,3,4-trimethylpentan-1-amine, 2,3-dimethylhexan-1-amine, 3,4-dimethylhexan-2-amine, 3,4,4-trimethylpentan-2-amine, 3-(aminomethyl)-2,3-dimethylpentane, 3-ethyl-2-methylpentan-2-amine, 3-(aminomethyl)-4-methylhexane, 2,2,3-trimethylpentan-1-amine, 3,3-dimethylhexan-1-amine, 2,2,3,3-tetramethylbutan-1-amine, 4-ethylhexan-3-amine, 3,3-dimethylhexan-2-amine, 3,3,4-trimethylpentan-2-amine, 3-(aminomethyl)-2,2-dimethylpentane, 5,5-dimethylhexan-3-amine, 3-methylheptan-4-amine, 2-methylheptan-4-amine, 2,2-dimethylhexan-3-amine, octan-4-amine, 4,4-dimethylhexan-3-amine, 2-methylheptan-4-amine, 6-methylheptan-3-amine, octan-4-amine, (2,2-dimethylcyclopentyl)methanamine, 2-ethylcyclohexan-1-amine, 5-dimethylcyclohexan-1-amine, cycloheptylmethanamine, 1-cyclohexylethan-1-amine, 2-cyclopentylpropan-1-amine, cyclooctanamine, 2,3-dimethylcyclohexan-1-amine, 2-cyclohexylethan-1-amine, 1-(methylcyclohexyl)methanamine, 4-ethylcyclohexan-1-amine, 2,6-dimethylcyclohexan-1-amine, and the like.

In embodiments, the stabilizer compound is selected from the group consisting of $n_1$-hexylamine, wherein $n_1$ is an integer in the range of 1-3 (i.e., 1-hexylamine, 2-hexylamine, or 3-hexylamine); $n_2$-heptylamine or $n_2$-octylamine, wherein $n_2$ is an integer in the range of 1-4; $n_3$-nonylamine or $n_3$-decylamine, wherein $n_3$ is an integer in the range of 1-5; or $n_4$-undecylamine or $n_4$-dodecylamine, wherein $n_4$ is an integer in the range of 1-6.

In some embodiments, the amine stabilizer is a secondary amine compound of formula VIII: $R^2NHR^3$, wherein $R^2$ and $R^3$ are independently selected from linear, branched, or cyclic alkyl group of 1-23 carbon atoms with the proviso that the total number of carbon atoms in $R^2$ and $R^3$ is at least 4, such as in the range of 4-24, 6-24, or 8-24 carbons. In some embodiments of formula VII, $R^2$ and $R^3$ are independently selected from the group consisting of methyl, ethyl, propyl, isopropyl, butyl, isobutyl, sec-butyl, tert-butyl, pentyl, cyclopentyl, methylcyclopentyl, hexyl, cyclohexyl, 1-, 2-, and 3-methylbutyl, 1,1-, 1,2-, or 2,2-dimethylpropyl, 1-ethyl-propyl, 1-, 2-, 3-, or 4-methylpentyl, 1,1-, 1,2-, 1,3-, 2,2-, 2,3-, or 3,3-dimethylbutyl, 1- or 2-ethylbutyl, 1-ethyl-1-methylpropyl, and 1,1,2- or 1,2,2-trimethylpropyl. In embodiments, $R^2$ and $R^3$ taken together provide at least 6 carbon atoms, at least 7 carbon atoms, or at least 8 carbon atoms.

Exemplary compounds include 6 carbon secondary amines such dipropylamine, ethyl(butyl)amine, (butan-2-yl)(ethyl)amine, tert-butyl(ethyl)amine, methyl(pentyl)amine, (2-methylbutyl)(methyl)amine, (2-methylpropyl)(ethyl)amine, methyl(3-methylbutyl)amine, and the like.

Exemplary compounds include 7 carbon secondary amines such as ethyl(pentyl)amine, butyl(propyl)amine, (butan-2-yl)(propyl)amine, tert-butyl(propan-2-yl)amine, hexyl(methyl)amine, (3,3-dimethylbutan-2-yl)(methyl)amine, 3,3-dimethylbutan-2-yl)(methyl)amine, (2-ethylbutyl)(methyl)amine, methyl(4-methylpentan-2-yl)amine, tert-butyl(propyl)amine, (2-methylpropyl)(propan-2-yl)amine, ethyl(3-methylbutyl)amine, butyl(propan-2-yl)amine, (2-methylpropyl)(propyl)amine, ethyl(pentan-2-yl)amine, ethyl(3-methylbutan-2-yl)amine, ethyl(pentan-3-yl)amine, ethyl(2-methylbutan-2-yl)amine, (butan-2-yl)(propan-2-yl)amine, methyl(2-methylpentyl)amine, methyl(3-methylpentan-2-yl)amine, ethyl(2-methylbutyl)amine, (2,2-dimethylpropyl)(ethyl)amine, (hexan-2-yl)(methyl)amine, and methyl(3-methylpentyl)amine, 2,3-dimethylpiperidine, 1,4-dimethylpiperidine, N-methylcyclohexanamine, and the like.

Exemplary compounds include 8 carbon secondary amines such as dibutylamine, (2-methylbutyl)(propyl)amine, ethyl(2-methylpentyl)amine, ethyl(3-methylpentan-2-yl)amine, (2-methylbutyl)(propan-2-yl)amine, (2, 3, 4, or 5-)ethyl(hexyl)amine, methyl(5-methylhexan-3-yl)amine, (pentan-3-yl)(propan-2-yl)amine, bis(2-methylpropyl)amine, (heptan-2-yl)(methyl)amine, tert-butyl(2-methylpropyl)amine. butyl(tert-butyl)amine, (heptan-4-yl)(methyl)amine, (3-methylbutyl)(propan-2-yl)amine, (butan-2-yl)(butyl)amine, heptyl(methyl)amine, bis(butan-2-yl)amine, (3,4-dimethylpentan-2-yl)(methyl)amine, 2,4,6-trimethylpiperidine, 3-(2-methylpropyl)pyrrolidine, 3,3-diethylpyrrolidine, 2-tert-butylpyrrolidine, N-methylcycloheptanamine, N-ethylcyclohexanamine, N,3-dimethylcyclohexan-1-amine.

Exemplary amine stabilizers also include cyclic secondary amines such as pyrrolidine and piperidine, and heterocyclic secondary amines such as morpholine.

Amine stabilizers of the disclosure also include "polyamines," which refers to compounds having more than one primary and/or secondary amine group. Polyamines include diamines, triamines, tetraamines, etc., wherein at least one of the amine groups, some of the amine groups, or all of the amine groups in the polyamine are primary and/or secondary amines. Exemplary polyamines can be of the formula X: $N_2(R^1)N_2$, wherein $R^1$ is a linear, branched, or cyclic divalent alkyl group, and the polyamine has at least 4 carbon atoms. Another exemplary polyamine is of the formula XI: $N_2((R^2)N(R^3))_x$, wherein $R^2$ is a linear, branched, or cyclic (divalent) alkylene group, and $R^3$ is a linear, branched, or cyclic (monovalent) alkyl group, x is an integer, such as in the range of 1 to 10, and the polyamine has at least 4 carbon atoms. Another exemplary polyamine is of the formula XII: $N_2((R^2)N(R^3))_xN_2$, wherein $R^2$ is a linear, branched, or cyclic (divalent) alkylene group, and $R^3$ is a linear, branched, or cyclic (monovalent) alkyl group, x is an integer, such as in the range of 1 to 10, and the polyamine has at least 4 carbon atoms. Compounds of any of Formulas X to XII can exclude certain chemistries, such as tertiary amine groups, quaternary amine groups, ethylenically unsaturated groups, or combinations thereof.

In some embodiments, the amine stabilizer is a diamine. One exemplary class of diamines is aryldiamines. Aryldiamines include two amine groups, with at least one primary or secondary amine group attached an aryl group in the compound. Exemplary aryldiamine species include ortho-phenylenediamine, meta-phenylenediamine, and para-phenylenediamine. The phenylenediamine can also be substituted at one or more positions on the aryl group that are not bonded to the amine groups. Exemplary substitution groups include linear and branched alkyl groups.

Amine stabilizers of the disclosure are generally in liquid or solid form at room temperature (25° C.). Some amine stabilizers with a number of carbon atoms or alkyl chain lengths of about 12 or may be in solid form at room temperature. In some embodiments, amine stabilizer compounds of the disclosure have melting points in the range of about −50° C. to about 100° C., in the range of about −30° C. to about 80° C., or in the range of about −10° C. to about 75° C. In some embodiments, amine stabilizer compounds of the disclosure have a boiling point of about 100° C. or greater, about 110° C. or greater, about 120° C. or greater, about 130° C. or greater, about 140° C. or greater, about 150° C. or greater, about 160° C. or greater, about 170° C. or greater, about 175° C. or greater, about 180° C. or greater, about 185° C. or greater, about 190° C. or greater, about 195° C. or greater, such as in the range of about 100° C. to about 300° C., or about 150° C. to about 250° C.

Amounts of the polymerization inhibitor compound, polymerization retarder, and amine stabilizer in a composition can be described in various ways, such as by a weight percentage (% wt.) of each component in the composition, or by molar amounts of the compounds. These compounds can also be described in terms of weight ratios, or in terms of relative amounts to one another, in a composition.

In some embodiments, in a composition the total combined amount (either measured as % wt. or molar amount) of the polymerization inhibitor and the polymerization compound is greater than the amount of the amine stabilizer. For example, the combined amount of inhibitor compound and the retarded compound can be greater than about 1.5×, greater than about 2×, greater than about 2.5×, greater than about 3×, greater than about 3.5×, greater than about 4×, greater than about 4.5×, or greater than about 5×, than the amount (% wt. or molar amount) of the polymerization inhibitor and the polymerization compound is greater of the amine stabilizer compound in a composition. For example, the combined amount of polymerization inhibitor and the polymerization retarded is in the range of about 1.5× to about 50×, or about 5× to about 25×, or about 5× to about 25×, greater than the amount (% wt. or molar amount) of the amine stabilizer in a composition.

In some embodiments, in a composition the polymerization retarder (quinone methide) is present in an amount greater than amine stabilizer. For example, the amount of polymerization retarder is greater than about 1.2×, greater than about 1.5×, greater than about 2×, greater than about 2.5×, greater than about 3×, greater than about 3.5×, or greater than about 4×, than the amount of the amine stabilizer compound in a composition. For example, the polymerization retarder is in the range of about 1.2× to about 25×, or about 2× to about 20×, or about 4× to about 15×, greater than the amount of the amine stabilizer in a composition.

In some embodiments, in a composition the polymerization inhibitor is present in an amount greater than amine stabilizer. For example, the amount of polymerization inhibitor is greater than about 1.1×, greater than about 1.3×, greater than about 1.6×, or greater than about 2×, than the amount of the amine stabilizer compound in a composition. For example, the polymerization inhibitor is in the range of about 1.1× to about 15×, or about 1.3× to about 10×, or about 1.6× to about 7×, greater than the amount of the stabilizer compound in a composition.

The polymerization inhibitor, polymerization retarder, and amine stabilizer in a composition can be present in a composition with a solvent, or a combination of solvents. A solvent or solvent combination can be chosen so that one or more of the polymerization inhibitor, polymerization retarder, and/or amine stabilizer are soluble in the solvent or solvent combination. If the amine stabilizer is a liquid at ambient conditions, the solvent can be chosen so that it is miscible with the amine stabilizer.

Optionally, a composition or method including the polymerization inhibitor having an N-to-O functionality, a polymerization retarder that is a quinone methide; and a stabilizer that is a primary or secondary amine compound can further include an oxygen-containing amine compound, such as an oxygen-containing amine compound of the following formula:

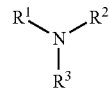

where $R^1$, $R^2$ and $R^3$ are independently selected from a) a carbon- and oxygen-containing group having 1-18 carbon atoms, b) a carbon-containing group having 1-18 carbon atoms, and c) —OH, with the proviso that at least one of $R^1$, $R^2$ and $R^3$ is a), wherein such compounds are disclosed in U.S. Provisional Application Ser. No. 62/697,744, filed Jul. 13, 2018, and PCT International Application No. PCT/US2019/041594, filed Jul. 12, 2018, the disclosures which are incorporated herein.

In embodiments, and in view of inhibitor, retarder, and amine stabilizer selections, the amine stabilizer may also function as a solvent, and can be used to solvate the inhibitor and retarder. In these embodiments, the amine stabilizer may be used at a desired amount in relation to the inhibitor and retarder, even in an amount that is greater than the inhibitor and retarder.

The composition can also include one or more solvents, and the one or more solvents can be different from the amine stabilizer. Useful solvents include any solvent in which a combination of inhibitor, retarder, and amine stabilizer are soluble or can be stably suspended. In some embodiments, a solvent or solvent combination can be selected from water-soluble or water-miscible solvents such glycol-based solvents and hydrophobic solvents such as aromatic solvents, paraffinic solvents, or mixtures of both.

Exemplary glycol solvents include, but are not limited, $C_1$-$C_8$ glycols such as ethylene glycol, propylene glycol, diethylene glycol, and triethylene glycol, ethers of such glycols such as diethylene glycol monobutyl ether, diethylene glycol monomethyl ether, diethylene glycol monoethyl ether, diethylene glycol monobutyl ether, triethylene glycol, triethylene glycol monomethyl ether, liquid polyethylene glycol, dipropylene glycol, dipropylene glycol monomethyl ether, dipropylene glycol monoethyl ether, and a low molecular weight polypropylene glycol and the like and combinations thereof. Commercial solvents such as Butyl Carbitol and Butyl CELLOSOLVE™, which contains primarily Butyl CARBITOL™, which consists primarily of ethylene glycol monobutyl ether may be used and are available from DOW.

Other exemplary hydrophobic solvents include heavy aromatic naphtha, toluene, ethylbenzene, and isomeric hexanes, and mixtures of two or more thereof.

In some embodiments, the solvent is selected from glycol and aromatic naphtha and combinations thereof.

The amount of one or more solvents in a composition that includes the polymerization inhibitor, polymerization retarder, and amine stabilizer is not particularly limited. In some embodiments, the amount of one or more solvents in the composition can be about 10 wt % to 50 wt %, for example, about 20 wt % to 50 wt %, or about 25 wt % to 50 wt %, or about 10 wt % to 40 wt %, or about 10 wt % to 30 wt %, or about 20 wt % to 40 wt %, or about 25 wt % to 40 wt % of the total composition.

In some embodiments the composition includes the polymerization inhibitor in an amount in the range of 5 to 50% (wt); the polymerization retarder in an amount in the range of 25 to 70% (wt); the amine stabilizer in an amount in the range of 0.5 to 15% (wt); and a solvent, or solvent combination, in an amount in the range of 10 to 50% (wt). In some embodiments the composition includes the polymerization inhibitor in an amount in the range of 7.5 to 40% (wt); the polymerization retarder in an amount in the range of 30 to 60% (wt); the amine stabilizer in an amount in the range of 1 to 12% (wt); and a solvent, or solvent combination, in an amount in the range of 15 to 45% (wt). In some embodiments the composition includes the polymerization inhibitor in an amount in the range of 10 to 30% (wt); the polymerization retarder in an amount in the range of 35 to 55% (wt); the amine stabilizer in an amount in the range of 3 to 9% (wt); and a solvent, or solvent combination, in an amount in the range of 20 to 40% (wt).

Compositions of the disclosure can be made using any desired method. However, in some embodiments it can be beneficial to add the amine stabilizer to the polymerization inhibitor prior to adding the polymerization retarder, or to add the amine stabilizer to the polymerization retarder, prior to adding the polymerization inhibitor.

As such the disclosure provides methods of preparing a composition for inhibiting monomer polymerization wherein a first composition is obtained that includes (i) the polymerization inhibitor (e.g., nitroxide polymerization inhibitor), and (ii) the amine stabilizer, and optionally a solvent, or solvent combination, and then adding (iii) a retarder compound that is a quinone methide to the first composition.

In another method, a first composition is obtained that includes (i) the retarder compound that is a quinone methide, and (ii) the amine stabilizer, and optionally a solvent, or solvent combination, and then adding (iii) a polymerization inhibitor (e.g., nitroxide polymerization inhibitor) to the first composition.

Yet another method of the disclosure involves combining simultaneously or sequentially (i) a retarder compound that is a quinone methide (ii) the polymerization inhibitor (e.g., nitroxide polymerization inhibitor), and (iii) the amine stabilizer to form a composition for inhibiting monomer polymerization.

For example, preparations of the amine stabilizer with either polymerization inhibitor or polymerization retarder, and optionally with solvent, can be obtained by a user, such as a commercial preparation, and then either the polymerization retarder or polymerization inhibitor is added subsequently, such as in a point of use procedure.

A composition that includes a mixture of the polymerization inhibitor, polymerization retarder, and amine stabilizer, and optionally with solvent, can be provided as a "shelf-stable" composition, and then subsequently used in a process to inhibit polymerization of monomers. Since the amine-based stabilizer of the invention can hinder antagonistic effects that may be seen when and inhibitor and retarder are combined, the mixture can be prepared and stored for an extended period of time (e.g., weeks, months, etc.) without a significant loss of antipolymerant activity. For example, methods of the disclosure can include a step of preparing a composition of polymerization inhibitor, polymerization retarder, amine stabilizer, and solvent, and then storing the composition for a period of time, such as in the range of 700 days to 36 months, and then using the composition in a process to inhibit polymerization of monomers.

Methods of abating the polymerization of monomers in a monomer-containing composition can be carried out by adding the components of the polymerization inhibitor, the polymerization retarder, and the amine stabilizer to a composition that includes a polymerizable monomer. The inhibitor and retarder inhibit the polymerization of the polymerizable monomer, and the presence of the amine stabilizer improves the antipolymerant properties of the inhibitor and retarder.

The polymerizable monomer that is subjected to polymerization inhibition can include a vinyl or ethylenically unsaturated group. For example, the components of the inhibitor, retarder, and amine stabilizer can be added to a composition that includes one or more of the following polymerizable monomers: acrylic acid, acrylonitrile, alkylated styrene, butadiene, chloroprene, divinylbenzene, ethyl acrylate, ethyl methacrylate, isoprene, methacrylic acid, methyl methacrylate, methyl acrylate, α-methylstyrene, methacrylonitrile, styrene, styrene sulfonic acid, vinyltoluene, and vinylpyridine.

The polymerizable monomer can be present in a crude mixture of compounds, a semi-refined mixture of compounds, or a fully-refined mixture of compounds. For example, the components of the inhibitor, retarder, and amine stabilizer may be added to a process stream that includes the polymerizable monomer. In methods, the components can be added before, during, or after, (or combinations thereof) a processing step, such as distillation, wherein compounds in the composition are separated from one another. The components can inhibit polymerization of monomer at any one or more stages in a processing system, and minimize fouling of equipment.

Alternatively, the components of the inhibitor, retarder, and amine stabilizer may be added to a process stream that includes a compound capable of the polymerizable monomer. For example, in compositions including a compound that is capable of forming a polymerizable monomer as an unwanted by-product, the presence of the inhibitor, retarder, and amine stabilizer can inhibit polymerization of the monomer if it does form as a by-product, and can therefore minimize fouling of equipment.

In some modes of practice, the inhibitor, retarder, and amine stabilizer are introduced into a monomer-containing composition to provide a desired amount of each reagent in the composition. The inhibitor, retarder, and amine stabilizer can be introduced simultaneously, such as delivered from a composition where the components are in mixture, or can be delivered individually or partially combined either sequentially, or in an overlapping manner. The resulting introduction of the components into the monomer-containing composition can provide the inhibitor, retarder, and amine stabilizer at desired concentrations. For example, at a polymerizable monomer concentration in the range of 50 to 200 ppm, the inhibitor can be introduced to provide an amount in the range of 15 to 60 ppm, the retarder can be introduced to provide an amount in the range of 25 to 100 ppm, and the stabilizer compound can be introduced to provide an amount in the range of 1 to 15 ppm. As another example, at a polymerizable monomer concentration in the range of 100 to 150 ppm, the inhibitor can be introduced to provide an amount in the range of 25 to 50 ppm, the retarder can be introduced to provide an amount in the range of 40 to 80 ppm, and the stabilizer compound can be introduced to provide an amount in the range of 2 to 12 ppm.

The term "fouling" refers to the formation of polymers, prepolymers, oligomer and/or other materials which would become insoluble in and/or precipitate from a stream and deposit on equipment under the conditions of operation of the equipment. In turn, the inhibitor, retarder, and amine stabilizer components and compositions of the disclosure can be referred to as "antifouling" as they inhibit or reduce such formation.

Optionally, the ability of the compositions of the disclosure to inhibit polymerization can be described relative to a composition that does not include the amine stabilizer. The effect of the amine stabilizer can be understood by measuring the formation of a polymer (e.g., polystyrene) in a monomer (e.g., styrene) composition over time, in the presence of an inhibitor/retarder/amine stabilizer composition versus an inhibitor/retarder composition (comparative). For example, a composition of the disclosure with inhibitor, retarder, and amine stabilizer inhibits polymerization of the monomer by more than two-fold, more than five-fold, or more than ten-fold, as compared to a composition with inhibitor and retarder compounds but without stabilizer compound under the same conditions.

The components of the inhibitor, retarder, and amine stabilizer can be used in conjunction with compositions containing polymerizable monomers and "process equipment" such as reactors, reactor beds, pipes, valves, distillation columns, trays, condensers, heat exchangers, compressors, fans, impellers, pumps, recirculators, inter-coolers, sensors, and the like, that are associated with the process and which may be subject to fouling by monomer polymerization. This term also includes sets of these components where more than one of the components is part of a "system."

In one preferred method of use, a composition of the disclosure with inhibitor, retarder, amine stabilizer, and solvent (e.g., glycol) is used with a process that involves a distillation tower that is used to separate and purify vinylic monomers. For example, in art-known processes ethylbenzene can be subjected to a catalytic dehydrogenation reaction which results in the formation of styrene. The reaction product containing styrene also contains other compounds such as aromatics like toluene and benzene, unreacted ethylbenzene, and other materials such as polymers. This mixture of compounds is generally fractionally distilled using one or more distillations towers. Typically, heat is used to help separate the components in the distillation tower. Following distillation the fractionated components can be separated into pure product streams with higher purity.

The inhibitor/retarder/amine stabilizer/solvent composition can be introduced into a stream leading from the reaction bed to the distillation tower, or can be directly added to the distillation tower. The inhibitor compositions can be added prior to heating the monomer composition or while heating the monomer composition in the distillation tower. In embodiments, the amine stabilizer has a boiling point that is greater that a desired compound (e.g., a monomer such as styrene) subject to distillation tower and during the distillation process the desired compound is separated from the amine stabilizer by virtue of temperature difference. In embodiments, the boiling point difference between the compound of interest and the amine stabilizer is about 10° C. or greater, about 15° C. or greater, about 20° C. or greater, about 25° C. or greater, about 30° C. or greater, about 35° C. or greater, about 40° C. or greater, about 45° C. or greater, or about 50° C. or greater.

Alternatively, or in addition to adding the inhibitor composition during the distillation process, the inhibitor composition can be added to a distillation effluent stream, such as a purified styrene stream.

The components of the inhibitor, retarder, and amine stabilizer can be used in conjunction with a "petroleum product" which refers to any hydrocarbon product obtained from a subterranean reservoir, any product derived therefrom, or any mixture thereof. Polymerizable monomers are found in or can be chemically derived from petroleum products. Nonlimiting examples of petroleum products include but are not limited to crude oil, reduced crude oil, crude distillate, heavy oil, or bitumen, hydrotreated oil, refined oil, byproducts of petroleum product processing such as pyrolysis, hydrotreating, or phase separation, or mixtures of two or more of these. A liquid petroleum product is a petroleum product that is substantially a liquid at 20° C.

The components of the inhibitor, retarder, and amine stabilizer can be added to or can be present in a "petroleum process stream" which refers to any petroleum product disposed within petroleum process equipment in fluid contact with an interior surface thereof. The petroleum process stream can include, or can be capable of forming as a by-product, one or more polymerizable monomer. The process stream may be substantially static, such as a petroleum product disposed in a settler (separator) or storage container for a selected period of contact, such as up to two years. The process stream may be substantially dynamic, such as a liquid petroleum product disposed within a pipe during transportation of the product from a first location to a second location. In some embodiments the process stream includes one or more additional components related to petroleum processing; such components are not particularly limited.

"Petroleum process equipment" or "petroleum process apparatus" refers to a manmade item having an interior surface including a metal, further wherein one or more petroleum products are fluidly contacted with the metal for any period of time and at any temperature further as determined by context. Petroleum process equipment includes items for removing petroleum products from a subterranean reservoir, for transporting one or more petroleum products from a first location to a second location, or for separating, refining, treating, isolating, distilling, reacting, metering, heating, cooling, or containing one or more petroleum products.

In embodiments, compositions including inhibitor, retarder, and amine stabilizer are thermolytically stable and have polymerization inhibitor and retarder activities in have properties in processing streams or other polymerizable monomer-containing compositions at temperatures of about 20° C. to about 400° C., for example about 100° C. to 400° C., or about 100° C. to 350° C., or about 100° C. to 300° C., or about 100° C. to 250° C., or about 100° C. to 200° C., or about 100° C. to 150° C.

In embodiments, compositions including inhibitor, retarder, and amine stabilizer can be introduced into a composition with a polymerizable monomer, such as a liquid petroleum process stream in a batch-wise, a continuous, or a semi-continuous manner. In some embodiments, the inhibitor, retarder, and amine stabilizer are introduced manually; and in other embodiments, their introduction is automated. In embodiments, the amount of the inhibitor, retarder, and amine stabilizer introduced over a selected unit of time is varied with a variable composition of the associated process stream. Such variability in dosing may be conducted manually by periodic testing of the process equipment interior surfaces, following by adjusting the amount of the composition up or down based on test results; or automatically by monitoring of one or more conditions within the interior of the petroleum process equipment and signaling the need to apply more composition to the process stream.

In some embodiments, the inhibitor, retarder, and amine stabilizer are added to a petroleum product that is a crude oil, a reduced crude oil, a heavy oil, a bitumen, a coker charge, a hydrotreater influent, a hydrotreater effluent, a flashed crude, a light cycle oil, or a diesel or naphtha refinery stream. In embodiments, the compounds are added to petroleum process equipment conventionally associated with the collecting, processing, transportation, or storage of one or more of crude oil, reduced crude oil, crude distillate, heavy oil, bitumen, coker charge, flashed crude, light cycle oil, or a diesel or naphtha refinery stream, including pipes and associated infrastructure used to fluidly connect process equipment items together to facilitate processing of a process stream disposed therein.

Equipment containing the polymerizable monomer-containing compositions that are treated with the inhibitor, retarder, and amine stabilizer can result in reduction or elimination of fouling interior surface of the equipment. In embodiments, fouling is measured as a relative increase in retention of solids within the treated composition compared to the retention of solids in untreated composition over the same time period. In embodiments, fouling is measured as a relative decrease in the weight or volume of precipitate arising from a selected period of contact of a treated process stream in an associated process equipment item, relative to the same period of contact of the process equipment with the corresponding untreated process stream. Stated differently, a reduction in fouling is a relative decrease in the measured weight or volume of solids deposited on or precipitated from process equipment contacted with the treated process stream over a selected period of time, when compared to the weight or volume of solids deposited or precipitated from an untreated process stream over the same period of time.

The inhibitor, retarder, and amine stabilizer can also inhibit unwanted polymerization and fouling of the process equipment in a primary fractionation process, light ends fractionation, non-aromatic halogenated vinyl fractionation, process-gas compression, dilution steam system, caustic tower, quench water tower, butadiene extraction, propane dehydrogenation, diesel and petrol fuel stabilization, olefin metathesis, styrene purification, hydroxyhydrocarbon purification, or delays the polymerization of resins and compositions comprising ethylenically unsaturated species.

The inhibitor, retarder, and amine stabilizer can be added at any given point in a process and at one or more locations. For example, the antifouling composition can be added directly at the inter-coolers or compressors or upstream of the inter-coolers or compressors. The inhibitor, retarder, and amine stabilizer can be added continuously or intermittently to the process equipment as required in order to inhibit or reducing fouling.

The inhibitor, retarder, and amine stabilizer can be introduced to desired systems by any suitable method. For example it may be added in neat or a dilute solution. In some embodiments, a composition containing the inhibitor, retarder, and amine stabilizer can be applied as a solution, emulsion, or dispersion that is sprayed, dripped, poured or injected into a desired opening within a system or onto the process equipment or process condensate. In some embodiments, the composition may be added with a wash oil or an attemperation water.

After introducing the composition to process equipment, treated process equipment can be observed to have less deposition on equipment than in process equipment without addition of the composition. Reduction or inhibition in fouling can be evaluated by any known method or test. In some embodiments, the reduction or inhibition of fouling can be accessed by measuring the time it takes for a sample with and without the antifoulant composition to gel. See the Experimental section for further details.

The following illustrative, non-limiting, examples are provided. Examples 1-5, 7-10, and 12-14 detail preparation of components of the experimental compositions or show formulations for comparative purposes.

Example 1

Figure 2:
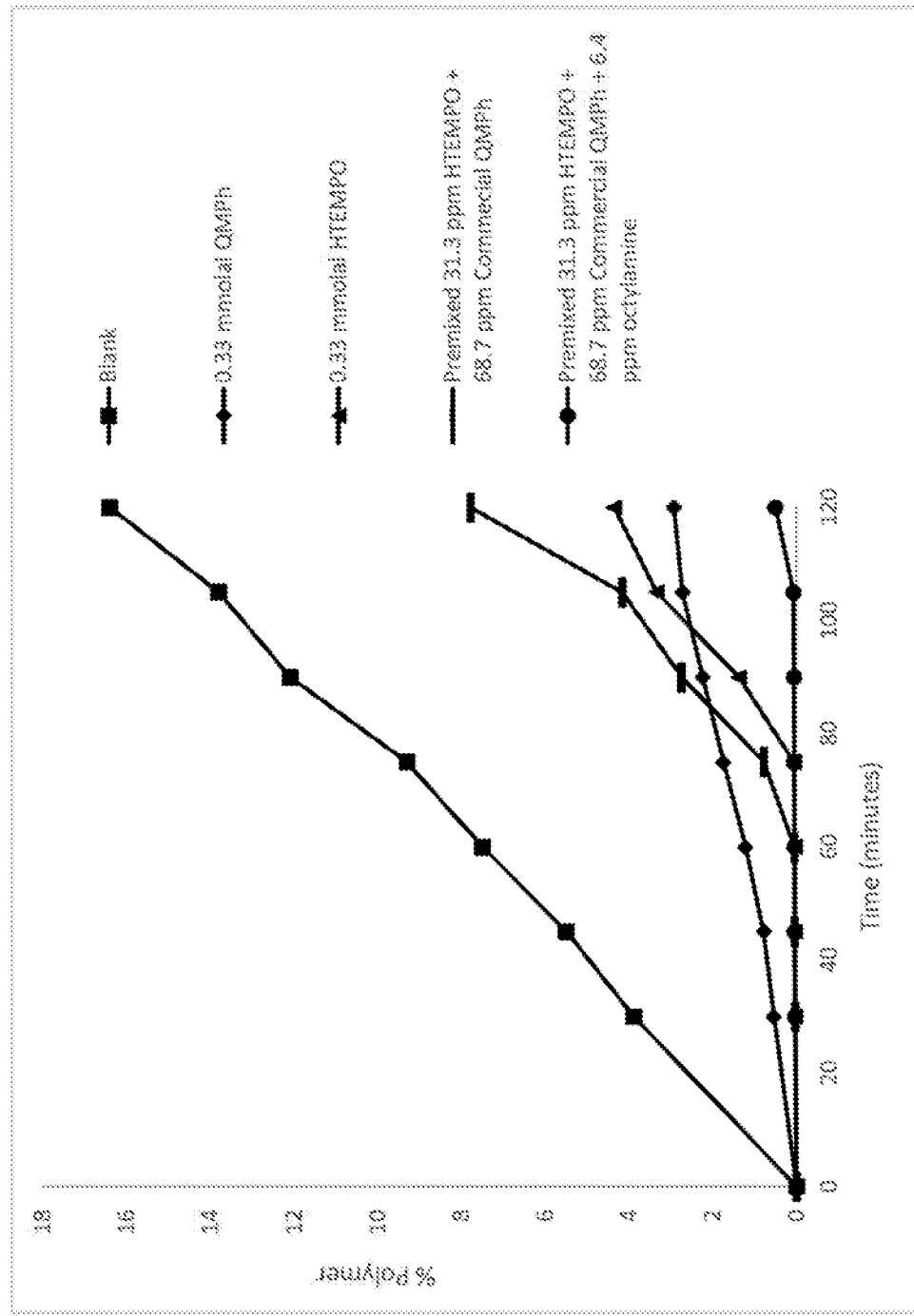
FIG. 2 is a graph of the formation of polystyrene in a styrene monomer solution over time in the presence of polymerization retarder and inhibitor introduced separately or in the presence of an amine stabilizer.

HTEMPO in Styrene 2.0 g of 4-hydroxy-2,2,6,6-tetramethylpiperidin-1-oxyl (HTEMPO) was dissolved in de-inhibited styrene to give 0.33 mmolar in 350 g of solution. The 4-tert-butylcatechol (TBC) stabilizer in the styrene had been removed just before the treatment composition. An alumina column was used for removal of said stabilizer. To each of twenty-four Ace Glass #15 threaded pressure tubes equipped with PTFE screw caps and fluoroelastomer (FETFE) 0-rings were charged 10 mL of the solution. For each test tube, the dissolved oxygen was purged out of the solutions by sparging with nitrogen for 2 minutes. Following the sparge, each tube was immediately sealed and the solution kept under a nitrogen headspace. The tubes were loaded into a heating block that had been preheated to 120° C. After 30 minutes, and every 15 minutes thereafter, four tubes were retrieved from the block and the polymerization reaction quenched by cooling in an ice bath. The cooled polymer solutions were immediately diluted with toluene. A proprietary method was also used to measure the polymer. See Tables 1 and 2 and FIGS. 1 and 2.

Example 2

7-Phenyl Quinone Methide (7-PhQM) in Styrene

For another comparative purpose, a solution of 100 ppm (0.33 mmolal) of 7-PhQM in 350 g of inhibitor-free styrene was prepared after which the antipolymerant performance was tested according to the procedure in Example 1. See Tables 1 and 2 and FIGS. 1 and 2.

Example 3

Co-Dosed HTEMPO and 7-Phenyl Quinone Methide in Styrene

For another comparative purpose, a solution of 68.7 ppm (0.33 mmolal) of 7-PhQM and 31.3 ppm of HTEMPO, in which they were added to 350 g of inhibitor-free styrene just before the test (co-injected), was prepared. Immediately thereafter, the antipolymerant performance was tested according to the procedure in Example 1. See Table 1 and FIG. 1.

Example 4

Untreated Styrene

Immediately after removing TBC from styrene, 10-mL aliquots of said styrene were charged into each of the afore-mentioned pressure tubes. After the dissolved oxygen was purged out of the solutions, polymerizations reactions and polymer analysis were conducted in accordance with the procedure in Example 1. See Tables 1 and 2 and FIGS. 1 and 2.

Example 5

HTEMPO, 7-PhQM, and Butyl Carbitol in Styrene

A composition consisting of 4.4 g of 7-phenyl quinone methide (7-PhQM), 3.6 g ethylbenzene, 2.0 g of 4-hydroxy-2,2,6,6-tetramethylpiperidin-1-oxyl (HTEMPO) and 2-(butoxymethoxy)ethan-1-ol (butyl carbitol) was prepared. After an incubation period of one week (premixed), it was screened to determine its antipolymerant performance. Immediately thereafter, the antipolymerant performance was tested according to the procedure in Example 1. See Table 2 and FIG. 2.

Example 6

HTEMPO, 7-PhQM, Butyl Carbitol, and 1-Octylamine in Styrene

As in Example 1, a composition consisting of 4.4 g of 7-phenyl quinone methide (7-PhQM), 3.0 g ethylbenzene, 2.0 g of 4-hydroxy-2,2,6,6-tetramethylpiperidin-1-oxyl (HTEMPO) and 2-(butoxymethoxy)ethanol (butyl carbitol) was prepared. To stabilize the composition, 0.6 g of 1-octylamine, were added. The incubated product was screened for the antipolymerant activity using the procedure in in Example 1. The presence of 1-octylamine caused the mixture of HTEMPO and 7-PhQM to have improved antipolymerant performance as evidenced by lower amount of polystyrene formed at all time points measured, and particularly at the later time points measured (+75 minutes) relative to controls. See Table 2 and FIG. 2.

TABLE 1

Performance of antipolymerants, as percent (weight for weight) polymer, when antipolymerants are co-injected into styrene.

| Time | Blank | 0.33 mmolal QMPh | 0.33 mmolal HTEMPO | Coinjected 31.3 ppm HTEMPO + 68.7 ppm Commercial QMPh | Coinjected 31.3 ppm HTEMPO + 68.7 ppm Inhouse QMPh |
|---|---|---|---|---|---|
| 0 | 0 | 0 | 0 | 0 | 0 |
| 30 | 3.89 | 0.541 | 0.0419 | 0.0318 | 0.0431 |
| 45 | 5.49 | 0.793 | 0.0506 | 0.0399 | 0.0520 |
| 60 | 7.5 | 1.22 | 0.0490 | 0.0549 | 0.0639 |
| 75 | 9.31 | 1.75 | 0.0667 | 0.0607 | 0.277 |
| 90 | 12.1 | 2.24 | 1.38 | 0.559 | 0.366 |
| 105 | 13.8 | 2.73 | 3.34 | 1.30 | 1.39 |
| 120 | 16.4 | 2.93 | 4.36 | 2.60 | 3.55 |

TABLE 2

Percent polymer (weight for weight) denoting the performance of amine-stabilized and amine-free single-package antipolymerant combinations.

| Time | Blank | 0.33 mmolal QMPh | 0.33 mmolal HTEMPO | Premixed 31.3 ppm HTEMPO + 68.7 ppm Commercial QMPh | Premixed 31.3 ppm HTEMPO + 68.7 ppm Commercial QMPh + 6.4 ppm octylamine |
|---|---|---|---|---|---|
| 0 | 0 | 0 | 0 | . | 0 |
| 30 | 3.89 | 0.541 | 0.0419 | 0.0412 | 0.0341 |
| 45 | 5.49 | 0.793 | 0.0506 | 0.0494 | 0.0447 |
| 60 | 7.5 | 1.22 | 0.0490 | 0.0558 | 0.0510 |
| 75 | 9.31 | 1.75 | 0.0667 | 0.787 | 0.0601 |
| 90 | 12.1 | 2.24 | 1.38 | 2.75 | 0.0675 |
| 105 | 13.8 | 2.73 | 3.34 | 4.16 | 0.0758 |
| 120 | 16.4 | 2.93 | 4.36 | 7.79 | 0.509 |

Example 7

4-Acetate TEMPOH in Styrene

Freshly prepared styrene (stabilizer-free) was dosed with 200 ppm of 1-hydroxy-2,2,6,6-tetramethylpiperidin-4-yl acetate (4-Acetate TEMPOH) followed by the kinetics study to determine the antipolymerant performance according to the procedure in Example 1. The results, % (w/w) of polystyrene as a function of time, are shown in Table 3.

Example 8

7-$CO_2$HQM in Styrene

Using freshly prepared styrene, a solution of 200 ppm of 7-Carboxylic Acid Quinone Methide/2-(3,5-di-tert-butyl-4-oxocyclohexa-2,5-dien-1-ylidene)acetic acid (7-$CO_2$HQM) was prepared. The antipolymerant performance was determined according to the procedure in Example 1. Table 3 shows the accumulation of polystyrene (% w/w) with respect to time.

TABLE 3

| Time (minutes) | 200 ppm 4-Acetate TEMPOH | 200 ppm $CO_2$HQM |
|---|---|---|
| 30 | 0.0169 | 0.0763 |
| 45 | 0.0251 | 0.441 |
| 60 | 0.0365 | 1.50 |
| 75 | 0.0550 | 3.60 |
| 90 | 0.0632 | 6.38 |
| 105 | 0.109 | 7.40 |
| 120 | 1.70 | 10.0 |

Example 9

QMPh in Styrene

As shown in prior examples, freshly prepared styrene was treated with 32 ppm of QMPh. The antipolymerant performance was determined demonstrated in Example 1. The resultant concentrations of polystyrene (% w/w) with respect to time are shown in Table 4.

Example 10

QMPh and 4-Acetate TEMPO in Styrene

A styrene solution of 22 ppm of QMPh and 10 ppm 4-Acetate TEMPO was prepared. Using the procedure in Example 1, the antipolymerant performance was determined; see Table 4 for results.

Example 11

QMPh, 4-Acetate TEMPO, and 2-Ethylhexylamine in Styrene

A styrene solution of 22 ppm of QMPh and 10 ppm 4-Acetate TEMPO stabilized with 6 ppm of 2-ethylhexylamine was prepared. The performance of this combination was determined according to the procedure in Example 1; see Table 4 for results. The presence of 2-ethylhexylamine caused the mixture of 4-Acetate TEMPO and QMPh to have improved antipolymerant performance as evidenced by lower amount of polystyrene formed at all time points measured relative to controls.

TABLE 4

| Time (minutes) | 32 ppm QMPh | 22 ppm QMPh + 10 ppm 4-Acetate TEMPO | 22 ppm QMPh + 10 ppm 4-Acetate TEMPO + 6 ppm 2-ethylhexylamine |
|---|---|---|---|
| 15 | 0.337 | 0.0396 | 0.0160 |
| 30 | 1.81 | 0.0744 | 0.0498 |
| 45 | 3.99 | 1.29 | 0.917 |
| 60 | 6.66 | 3.44 | 3.04 |
| 75 | 8.83 | 6.10 | 5.30 |
| 90 | 11.4 | 7.98 | 6.55 |

Example 12

QMPh in Styrene

A solution of 2.57 mmolal of QMPh was prepared using freshly purified styrene. The antipolymerant performance was determined using the procedure in Example 1; see Table 5 for results.

Example 13

QMPh and TIPA in Styrene

For comparison, a solution of 2.31 mmolal of QMPh, which was 90% (mole/mole) of the QMPh concentration in Example 12, and 0.257 mmolal triisopropanolamine (TIPA) (10% mole/mole of the QMPh concentration in Example 12) was prepared using freshly purified styrene. The procedure in Example 1 was used to determine the performance of this combination; see Table 5 for results.

Example 14

QMPh and 4-Acetate TEMPOH in Styrene

As in Example 13, a solution of 2.31 mmolal of QMPh and 0.257 mmolal 4-Acetate TEMPOH was prepared using freshly purified styrene. The performance of this illustrative combination was determined according to the procedure in Example 1. The effect in the performance of this combination is shown in Table 5.

Example 15

QMPh, HTEMPOH, and Dipropylamine in Styrene

Another illustrative example was carried by preparing a styrene solution of a combination of 2.31 mmolal of QMPh, 0.173 mmolal 2,2,6,6-tetramethylpiperidine-1,4-diol (HTEMPOH) and 0.0719 mmolal (71.9 μmolal) dipropylamine. The performance of this illustrative combination was determined using the procedure in Example 1. The effect of the amine in the performance of this combination is shown in Table 5. The presence of dipropylamine caused the mixture of HTEMPOH and QMPh to have improved antipolymerant performance as evidenced by lower amount of polystyrene formed at all time points measured relative to controls.

TABLE 5

Example of synergistic combination of 4-Acetate TEMPO and QMPh and an amine.

| Time (minutes) | 2.57 mmolal QMPh | 2.31 mmolal QMPh + 0.257 mmolal TIPA | 2.31 mmolal QMPh + 0.257 mmolal 4-Acetate TEMPOH | 2.31 mmolal QMPh + 0.173 mmolal HTEMPOH + 71.9 μmolal Dipropylamine |
|---|---|---|---|---|
| 40 | 0.270 | 0.174 | 0.0528 | 0.0519 |
| 80 | 0.797 | 0.797 | 0.142 | 0.0745 |
| 120 | 1.17 | 1.31 | 0.690 | 0.306 |
| 160 | 2.08 | 1.95 | 1.44 | 0.788 |
| 200 | 2.50 | 2.89 | 2.79 | 1.32 |
| 240 | 7.66 | 3.73 | 3.73 | 2.90 |

What is claimed is:

1. A composition for inhibiting monomer polymerization comprising:
    an inhibitor compound that comprises an N-to-O bond;
    a retarder compound that is a quinone methide;
    a stabilizer compound comprising a primary or secondary amine group; and
    an organic solvent;
wherein the inhibitor is in an amount in the range of 5 to 50% (wt), the retarder is in an amount in the range of 25 to 70% (wt), the stabilizer compound is in an amount in the range of 0.5 to 15% (wt), and the organic solvent is in an amount in the range of 10 to 50% (wt).

2. The composition of claim 1 wherein the stabilizer is an alkylamine that comprises a linear, branched, heterocyclic, or cyclic alkyl group.

3. The composition of claim 1, wherein the stabilizer compound has at least 4 carbons.

4. The composition of claim 3 wherein the stabilizer compound is of formula $R^1NH_2$, wherein $R^1$ is a linear, branched, or cyclic alkyl group of 4-24 carbons.

5. The composition of claim 4 wherein the stabilizer compound is selected from the group consisting of hexylamine, heptylamine, ethylhexylamine, octylamine, nonylamine, decylamine, undecylamine, and dodecylamine.

6. The composition of claim 1 wherein the stabilizer compound is of formula $R^2NHR^3$, wherein $R^2$ and $R^3$ are independently selected from linear, branched, or cyclic alkyl groups of 1-23 carbon atoms with the proviso that the total number of carbon atoms in $R^2$ and $R^3$ is in the range of 4-24 carbons.

7. The composition of claim 1 wherein the stabilizer compound is a cyclic secondary amine, a heterocyclic secondary amine, an arylamine, an aryldiamine, or a polyamine, or a polyalkylpolyamine.

8. The composition of claim 1 wherein the inhibitor compound is selected from the group consisting of nitroxide-, amine oxide-, hydroxylamine-, nitroso-, and nitrone-containing compounds.

9. The composition of claim 8 wherein the inhibitor compound is a nitroxide- or hydroxylamine-containing compound of the following formula:

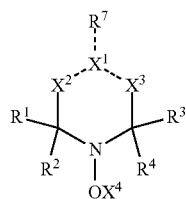

wherein $R^1$, $R^2$, $R^3$, and $R^4$ are independently selected from H, C1-C22 linear, branched, cyclic alkyl, and aryl, wherein $X^2 \ldots X^1$ and $X^1 \ldots X^3$ is C—C or C=C, wherein $X^4$ is H or an unpaired electron, wherein $X^1 \ldots R^7$ is selected from C—O, C=O, C—H, C—$OR^8$, and C—$OC(O)R^8$, and wherein $R^8$ is selected from H, and C1-C22 linear, branched, and cyclic alkyl, and C1-C22 aryl, aryl alkyl, and alkyl aryl, or bis- or tris- compounds according to Formulas IV and V respectively:

Formula IV

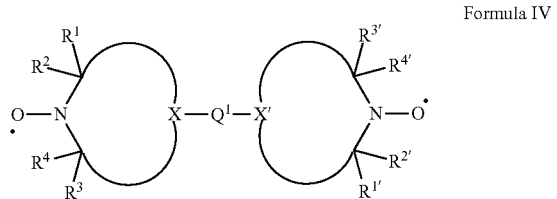

Formula V

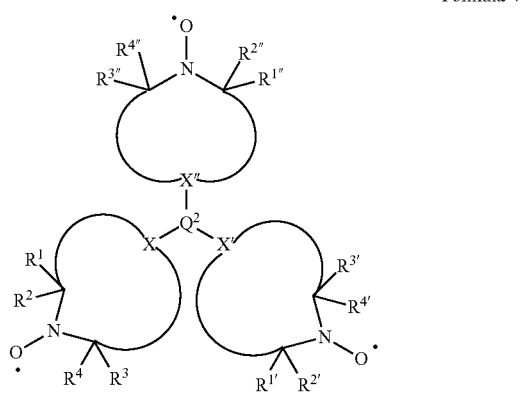

wherein $R^{1'}$, $R^{2'}$, $R^{3'}$, and $R^{4'}$, and $R^{2''}$, $R^{3''}$, and $R^{4''}$, have the same definitions as $R^1$, $R^2$, $R^3$, and $R^4$ of formula III, respectively, and X' and X'', have the same definitions as X of formula III, and wherein $Q^1$ can is a divalent linking group formed from a compound selected from the group consisting of diacids, diesters, diamides, diols, diamines, and $Q^2$ is a trivalent linking group formed from a compound selected from the group consisting of triacids, triols, amines, and triazines.

10. The composition of claim 9 wherein the inhibitor compound is:

(a) a nitroxide-containing compound comprising a piperidonoxyl group having the following formula:

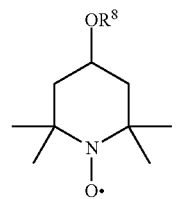

wherein $R^8$ is selected from H, and C1-C22 alkyl, aryl, aryl alkyl and alkyl aryl, and optionally selected from the group consisting of: 1-oxyl-2,2,6,6-tetramethylpiperin-4-ol, 4-methoxy-2,2,6, 6-tetramethylpiperidin-1-oxy, 4-ethoxy-2, 2,6,6-tetramethylpiperidin-1-oxy, 4-propoxy-2,2,6, 6-tetramethylpiperidin-1-oxy, 4-butoxy-2,2,6,6-tetramethylpiperidin-1-oxy, 4-pentoxy-2,2,6, 6-tetramethylpiperidin-1-oxy, 4-hexyloxy-2,2,6,6-tetramethylpiperidin-1-oxy, 4-heptyloxy-2,2,6, 6-tetramethylpiperidin-1-oxy, 4-octyloxy-2,2,6,6-tetramethylpiperidin-1-oxy, 4-nonyloxy-2,2,6, 6-tetramethylpiperidin-1-oxy, 4-decyloxy-2,2,6,6-tetramethylpiperidin-1-oxy, 4-undecyloxy-2,2,6, 6-tetramethylpiperidin-1-oxy, 4-dodecyloxy-2,2,6,6-tetramethylpiperidin-1-oxy, 4-tridecyloxy-2,2,6,6-tetramethylpiperidin-1-oxy, 4-tetradecyloxy-2,2,6,6-tetramethylpiperidin-1-oxy, 4-pentadecyloxy-2,2,6,6-tetramethylpiperidin-1-oxy, 4-hexadecyloxy-2,2,6, 6-tetramethylpiperidin-1-oxy, 4-heptadecyloxy-2,2,6,6-tetramethylpiperidin-1-oxy, 4-octadecyloxy-2,2,6,6-tetramethylpiperidin-1-oxy, 4-nodecyloxy-2,2,6,6-tetramethylpiperidin-1-oxy, 4-decyloxy-2,2,6,6-tetramethylpiperidin-1-oxy, 4-icosyloxy-2,2,6,6-tetramethylpiperidin-1-oxy, 4-henicosyloxy-2,2,6,6-tetramethylpiperidin-1-oxy, 4-docosyloxy-2,2,6, 6-tetramethylpiperidin-1-oxy, 4-(phenoxy)2,2,6,6-tetramethylpiperidin-1-oxy, 4-(benzyloxy)-2, 2,6,6-tetramethylpiperidin-1-oxy, and 2,2,6,6-tetramethyl-4-(naphthalen-2-yloxy)piperidin-1-oxy;

(b) a nitroxide-containing compound comprising a piperidinol group of the following formula:

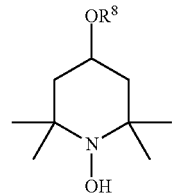

wherein $R^8$ is selected from H, and C1-C22 alkyl, aryl, aryl alkyl, and alkyl aryl, and optionally selected from the group consisting of 2,2,6,6-tetramethylpiperin-1,4-diol, 4-methoxy-2,2,6, 6-tetramethylpiperidin-1-ol, 4-ethoxy-2,2, 6,6-tetramethylpiperidin-1-ol, 4-propoxy-2,2,6, 6-tetramethylpiperidin-1-ol, 4-butoxy-2,2,6,6-tetramethylpiperidin-1-ol, 4-pentoxy-2,2,6, 6-tetramethylpiperidin-1-ol, 4-hexyloxy-2,2,6,6-tetramethylpiperidin-1-ol, 4-heptyloxy- 2,2,6, 6-tetramethylpiperidin-1-ol, 4-octyloxy-2,2,6,6-tetramethylpiperidin-1-ol, 4-nonyloxy-2,2,6, 6-tetramethylpiperidin-1-ol, 4-decyloxy-2,2,6,6-tetramethylpiperidin-1-ol, 4-undecyloxy-2,2,6, 6-tetramethylpiperidin-1-ol, 4-dodecyloxy-2,2,6,6-tetramethylpiperidin-1-ol, 4-tridecyloxy-2,2,6, 6-tetramethylpiperidin-1-ol, 4-tetradecyloxy-2,2,6,6-tetramethylpiperidin-1-ol, 4-pentadecyloxy-2, 2,6,6-tetramethylpiperidin-1-ol, 4-hexadecyloxy-2,2,6,6-tetramethylpiperidin-1-ol, 4-heptadecyloxy-2,2,6,6-tetramethylpiperidin-1-ol, 4-octadecyloxy-2,2,6,6-tetramethylpiperidin-1-ol, 4-nodecyloxy-2,2,6,6-tetramethylpiperidin-1-ol, 4-decyloxy-2,2, 6,6-tetramethylpiperidin-1-ol, 4-icosyloxy-2,2,6,6-tetramethylpiperidin-1-ol, 4-henicosyloxy-2,2,6,6-tetramethylpiperidin-1-ol, 4-docosyloxy-2,2,6,6-tetramethylpiperidin-1-ol, 4-(phenoxy)-2,2,6,6-tetramethylpiperidin-1-ol, 4-(benzyloxy)-2,2, 6,6-tetramethylpiperidin-1-ol, and 2,2,6,6-tetramethyl-4-(naphthalen-2-yloxy)piperidin-1-ol;

(c) a nitroxide-containing compound comprising a piperidinoxy group of the following formula:

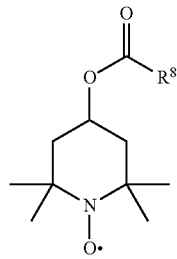

wherein $R^8$ is selected from H, and C1-C22 alkyl, aryl, aryl alkyl, and alkyl aryl, and optionally selected from the group consisting of 1-oxyl-2,2,6,6-tetramethylpiperidin-4-yl acetate, 1-oxyl-2, 2,6,6-tetramethylpiperidin-4-yl propanoate, 1-oxyl-2,2,6,6-tetramethylpiperidin-4-yl butyrate, 1-oxyl-2,2,6,6-tetramethylpiperidin-4-yl pentanoate, 1-oxyl-2,2,6,6-tetramethylpiperidin-4-yl hexanoate, 1-oxyl-2,2,6,6-tetramethylpiperidin-4-yl heptanoate, 1-oxyl-2,2,6, 6-tetramethylpiperidin-4-yl octanoate, 1-oxyl-2,2,6,6-tetramethylpiperidin-4-yl nonanoate, 1-oxyl-2, 2,6,6-tetramethylpiperidin-4-yl decanoate, 1-oxyl-2,2,6,6-tetramethylpiperidin-4-yl undecanoate, 1-oxyl-2,2,6,6-tetramethylpiperidin-4-yl dodecanoate, 1-oxyl-2,2,6, 6-tetramethylpiperidin-4-yl 2-ethylhexanoate, 1-oxyl-2,2,6, 6-tetramethylpiperidin-4-yl stearate, 1-oxyl-2,2,6,6-tetramethylpiperidin-4-yl benzoate, 1-oxyl-2,2,6,6-tetramethylpiperidin-4-yl palmitoate, 1-oxyl-2,2,6,6-tetramethylpiperidin-4-yl behenoate, and 1-oxyl-2,2,6, 6-tetramethylpiperidin-4-yl 4-tert-butylbenzoate; or (d) a nitroxide-containing compound comprising a piperidinol group of the following formula:

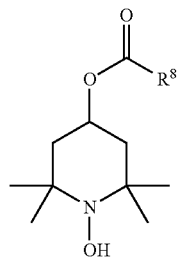

wherein $R^8$ is selected from H, and C1-C22 alkyl, aryl, aryl alkyl, and alkyl aryl and optionally selected from the group consisting of 1-hydroxy-2,2,6,6-tetramethylpiperidin-4-yl acetate, 1-hydroxy-2,2,6,6-tetramethylpiperidin-4-yl propanoate, 1-hydroxy-2,2,6,6-tetramethylpiperidin-4-yl butyrate, 1-hydroxy-2,2,6,6-tetramethylpiperidin-4-yl pentanoate, 1-hydroxy-2,2,6, 6-tetramethylpiperidin-4-yl hexanoate, 1-hydroxy-2,2,6,6-tetramethylpiperidin-4-yl heptanoate, 1-hydroxy-2,2,6,6-tetramethylpiperidin-4-yl octanoate, 1-hydroxy-2,2,6,6-tetramethylpiperidin-4-yl nonanoate, 1-hydroxy-2,2,6,6-tetramethylpiperidin-4-yl decanoate, 1-hydroxy-2,2,6, 6-tetramethylpiperidin-4-ylundecanoate, 1-hydroxy-2,2,6,6-tetramethylpiperidin-4-yl dodecanoate, 1-hydroxy-2,2,6,6-tetramethylpiperidin-4-yl 2-ethylhexearate, 1-hydroxy-2,2,6, 6-tetramethylpiperidin-4-yl stearate, 1-hydroxy-2,2,6,6-tetramethylpiperidin-4-yl benzoate, 1-hydroxy-2,2,6,6-tetramethylpiperidin-4-yl palmitoate, 1-hydroxy-2,2,6,6-tetramethylpiperidin-4-yl behenoate, 1-hydroxy-2,2,6,6-tetramethylpiperidin-4-yl 4-tert-butylbenzoate.

11. The composition of claim 9 wherein the inhibitor is a nitroxide-containing compound selected from the group consisting of 2,2,6,6-tetramethylpiperidinyl-1-oxyl (TEMPO), 4-hydroxy-2,2,6,6-tetramethylpiperidinyl-1-oxyl (HTMPO), 4-oxo-2,2,6, 6-tetramethylpiperidinyl-1-oxyl (OTEMPO), and 1-hydroxy-2,2,6,6-tetramethylpiperidin-4-one, or a combination thereof.

12. The composition of claim 1 wherein the quinone methide retarder has a formula of:

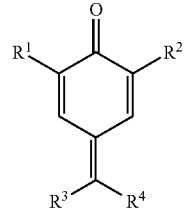

wherein $R^1$ and $R^2$ are independently selected from C4-C18 alkyl, C5-C12 cycloalkyl, phenyl, and C7-C15 cycloalkyl, wherein $R^3$ and $R^4$ are independently selected from —H, C1-C18 alkyl, phenyl, substituted phenyl, C5-C12 cycloalkyl, —CN, —COOH, —C=$CR^5$, —C≡$CR^5$, —$COOR^5$, —$COR^5$, —$OCOR^5$, —$CONR^5$, wherein $R^5$ is selected from H, C1-C18 alkyl, C5-C12 cycloalkyl, phenyl, and C7-C15 cycloalkyl, and substituted phenyl.

13. The composition of claim 1 wherein the inhibitor is in an amount in the range of 10 to 30% (wt); the retarder is in an amount in the range of 35 to 55% (wt); the stabilizer compound is in an amount in the range of 3 to 9% (wt); and the organic solvent is in an amount in the range of 20 to 40% (wt).

14. A method of preparing a composition for inhibiting monomer polymerization comprising:
obtaining a first composition comprising (i) an inhibitor compound that comprises an N-to-O bond (ii) a stabilizer compound comprising a primary or secondary amine group, and then adding (iii) a retarder compound that is a quinone methide to the first composition to form a second composition;
obtaining a first composition comprising (i) a retarder compound that is a quinone methide (ii) a stabilizer compound comprising a primary or secondary amine group, and then adding (iii) an inhibitor compound that comprises an N-to-O bond to the first composition to form a second composition; or combining simultaneously or sequentially (i) a retarder compound that is a quinone methide (ii) an inhibitor compound that comprises an N-to-O bond, and (iii) a stabilizer compound comprising a primary or secondary amine group to form a composition for inhibiting monomer polymerization to form a second composition;

wherein the second composition comprises the inhibitor in an amount in the range of 5 to 50% (wt), the retarder in an amount in the range of 25 to 70% (wt), the stabilizer compound in an amount in the range of 0.5 to 15% (wt), and an organic solvent in an amount in the range of 10 to 50% (wt), or wherein the second composition comprises the inhibitor in an amount in the range of 15 to 60 ppm, the retarder in an amount in the range of 25 to 100 ppm, and the stabilizer compound is in an amount in the range of 1 to 15 ppm, and the second composition further comprises a polymerizable monomer is in an amount in the range of 50 to 200 ppm.

15. A method for inhibiting the polymerization of monomers in a monomer-containing composition, the method comprising adding components comprising:
an inhibitor compound that comprises an N-to-O bond;
a retarder compound that is a quinone methide; and
a stabilizer compound comprising a primary or secondary amine group to a second composition comprising polymerizable monomer or capable of forming a polymerizable monomer, wherein the first composition inhibits the polymerization of the polymerizable monomer;

wherein adding forms a treated second composition wherein polymerizable monomer is in an amount in the range of 50 to 200 ppm, the inhibitor is in an amount in the range of 15 to 60 ppm, the retarder is in an amount in the range of 25 to 100 ppm, and the stabilizer compound is in an amount in the range of 1 to 15 ppm.

16. The method of claim 15 wherein the polymerizable monomer is selected from the group consisting of acrylic acid, acrylonitrile, alkylated styrene, butadiene, chloroprene, divinylbenzene, ethyl acrylate, ethyl methacrylate, isoprene, methacrylic acid, methyl methacrylate, methyl acrylate, a-methylstyrene, methacrylonitrile, styrene, styrene sulfonic acid, vinyltoluene, and vinylpyridine.

17. The method of claim 15 which is performed during purification or processing of one or more components of the second composition.

18. The method of claim 15 wherein after addition of the first composition, the second composition is subject to a distillation step and the stabilizer compound has a boiling point that is greater than the polymerizable monomer.

19. The composition of claim 1 comprising an organic solvent in an amount in the range of 15 to 50% (wt).

20. A composition for inhibiting monomer polymerization comprising:
an inhibitor compound that comprises an N-to-O bond;
a retarder compound that is a quinone methide;
a stabilizer compound of: formula $R^1NH_2$, wherein $R^1$ is a linear, branched, or cyclic alkyl group of 4-24 carbons, or formula $R^2NHR^3$, wherein $R^2$ and Ware independently selected from linear, branched, or cyclic alkyl groups of 1-23 carbon atoms with the proviso that the total number of carbon atoms in $R^2$ and $R^3$ is in the range of 4-24; and
and organic solvent
wherein the inhibitor is in an amount in the range of 5 to 50% (wt), the retarder is in an amount in the range of 25 to 70% (wt), the stabilizer compound is in an amount in the range of 0.5 to 15% (wt), and the organic solvent is in an amount in the range of 10 to 50% (wt).

21. The composition of claim 20 wherein the inhibitor compound is present in an amount greater than the stabilizer compound.

22. The composition of claim 20 wherein a combined amount of the inhibitor compound and the retarder compound is in the range of 1.5 times to 50 times greater than the amount of the stabilizer compound.

* * * * *